US 6,613,932 B1

(12) United States Patent
Sato et al.

(10) Patent No.: US 6,613,932 B1
(45) Date of Patent: Sep. 2, 2003

(54) PROSTAGLANDIN DERIVATIVES

(75) Inventors: Fumie Sato, Kanagawa (JP); Tohru Tanami, Tokyo (JP); Hideo Tanaka, Tokyo (JP); Naoya Ono, Tokyo (JP); Makoto Yagi, Tokyo (JP); Hitomi Hirano, Tokyo (JP)

(73) Assignees: Taisho Pharmaceutical Co., Ltd., Tokyo (JP); Fumie Sato, Kanagawa (JP)

( * ) Notice: Subject to any disclaimer, the term of this patent is extended or adjusted under 35 U.S.C. 154(b) by 0 days.

(21) Appl. No.: 10/070,752

(22) PCT Filed: Sep. 8, 2000

(86) PCT No.: PCT/JP00/06161

§ 371 (c)(1),
(2), (4) Date: Mar. 11, 2002

(87) PCT Pub. No.: WO01/19789

PCT Pub. Date: Mar. 22, 2001

(30) Foreign Application Priority Data

Sep. 10, 1999 (JP) .............................. 11-256726
Mar. 21, 2000 (JP) ........................ 2000-079147

(51) Int. Cl.[7] ...................... C07C 69/74; C07C 403/00; A61K 31/5575
(52) U.S. Cl. ......................... 560/1; 560/118; 562/500; 514/59
(58) Field of Search ........................ 560/118; 562/500

(56) References Cited

U.S. PATENT DOCUMENTS

| | | |
|---|---|---|
| 4,029,681 A | 6/1977 | Smith |
| 4,131,738 A | 12/1978 | Smith |
| 4,189,597 A * | 2/1980 | Weiss et al. ............... 560/118 |

FOREIGN PATENT DOCUMENTS

| | | |
|---|---|---|
| JP | 52-100446 | 8/1977 |
| WO | WO 88-05042 | 7/1988 |
| WO | WO 00-61550 | 10/2000 |

OTHER PUBLICATIONS

International Search Report.

* cited by examiner

Primary Examiner—Robert Gerstl
(74) Attorney, Agent, or Firm—Sughrue Mion, PLLC

(57) ABSTRACT

A prostaglandin derivative represented by the formula:

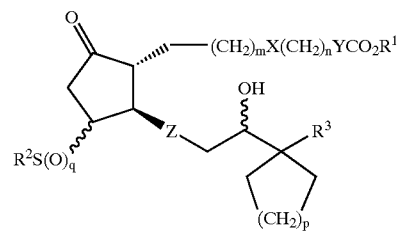

[wherein X is $CH_2$, O or $S(O)_{q1}$, Y is an ethylene group, a vinylene group, an ethynylene group, $O(CH_2)_{t1}$ or $S(O)_{q2}(CH_2)_{t1}$, Z is an ethylene group, a vinylene group or an ethynylene group, $R^1$ is a hydrogen atom, a $C_{1-10}$ alkyl group or a $C_{3-10}$ cycloalkyl group, $R^2$ is a $C_{1-10}$ alkyl group, a $C_{2-10}$ alkenyl group, a $C_{2-10}$ alkynyl group, a $C_{3-10}$ cycloalkyl group, a $C_{1-5}$ alkyl-$C_{3-10}$ cycloalkyl group, a $C_{3-10}$ cycloalkyl-$C_{1-5}$ alkyl group, a hydroxy-$C_{1-5}$ alkyl group, a halogeno-$C_{1-5}$ alkyl group, a $C_{1-5}$ alkoxy-$C_{1-5}$ alkyl group, a $C_{2-4}$ alkoxycarbonyl-$C_{1-5}$ alkyl group, a carboxyl-$C_{1-5}$ alkyl group, a cyano-$C_{1-5}$ alkyl group, a $C_{1-5}$ alkyl group substituted with a group represented by the formula: $—NR^7R^8$, an acyl group, a group represented by the formula: $—(CH_2)_{t2}CH(NH_2)COOR^9$, etc., and $R^3$ is a hydrogen atom, a $C_{1-10}$ alkyl group, etc.], a pharmaceutically acceptable salt thereof or a hydrate thereof.

Novel prostaglandin derivatives of the present invention have an excellent action in inhibiting the growth of vascular smooth muscle, and are useful as drugs for prevention or treatment of the restenosis after PTCA, etc.

6 Claims, No Drawings

PROSTAGLANDIN DERIVATIVES

TECHNICAL FIELD

The present invention relates to novel prostaglandin derivatives, pharmaceutically acceptable salts thereof and hydrates thereof.

BACKGROUND ART

Since prostaglandin (PG) exhibits various important physiological actions in a trace amount, the biological activities of a great number of natural PGs and synthesized PG derivatives have been investigated with the intention of a practical use as medicines and have been reported in many literatures, for example, Japanese Patent Kokai No. 52-100446 and U.S. Pat. No. 4,131,738. Natural PGs and PG derivatives have biological actions such as a vasodilating action, a prophlogistic action, an inhibitory action of blood platelet aggregation, a uterine muscle contraction action, an intestine contraction action or a lowering action of intraocular pressure, and are useful for treatment or prevention of myocardial infarction, angina pectoris, arteriosclerosis, hypertension or duodenal ulcer, and further useful for labor induction, artificial termination of pregnancy, etc.

On the other hand, percutaneous transluminal coronary angioplasty (PTCA) has low invasiveness to the patient as a therapeutic modality of ischemic heart diseases and has an excellent initial treatment effect, therefore, it is a plasty which recently has rapidly been developed. However, there has been an unsolved drawback of causing restenosis of coronary artery at a frequency of 30–40% within a few months after PTCA. The compounds which can control not only the migration from intima to mesothelium of vascular smooth muscle cells deeply associating with the onset of restenosis but also their growth in the mesothelium are greatly expected as drugs for prevention of the restenosis caused after PTCA. However, no clinically available drugs have been found.

An object of the present invention is to provide novel PG derivatives which have an excellent action in inhibiting the growth of vascular smooth muscle and are greatly expected as drugs for prevention or treatment of the restenosis after PTCA.

DISCLOSURE OF THE INVENTION

As a result of the continued extensive studies, the present inventors have found that novel prostaglandin derivatives having an alkylthio group, an arylthio group or the like at the 11-position represented by the following Formula (I) achieve the above-objects, and thereby the present invention has been accomplished.

That is, the present invention is directed to a prostaglandin derivative represented by Formula (I):

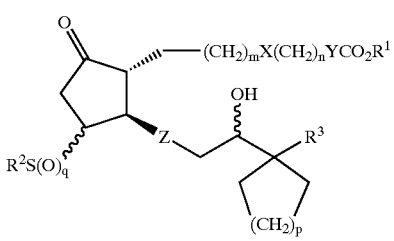

(I)

[wherein X is $CH_2$, O or a group represented by the formula: $S(O)_{q1}$ (wherein q1 is an integer of 0 to 2), Y is an ethylene group, a vinylene group, an ethynylene group or a group represented by the formula: $O(CH_2)_{t1}$ or $S(O)_{q2}(CH_2)_{t1}$ (wherein q2 is an integer of 0 to 2, and t1 is an integer of 1 to 3), Z is an ethylene group, a vinylene group or an ethynylene group, $R^1$ is a hydrogen atom, a $C_{1-10}$ alkyl group or a $C_{3-10}$ cycloalkyl group, $R^2$ is a $C_{1-10}$ alkyl group, a $C_{2-10}$ alkenyl group, a $C_{2-10}$ alkynyl group, a $C_{3-10}$ cycloalkyl group, a $C_{1-5}$ alkyl-$C_{3-10}$ cycloalkyl group, a $C_{3-10}$ cycloalkyl-$C_{1-5}$ alkyl group, a hydroxy-$C_{1-5}$ alkyl group, a halogeno-$C_{1-5}$ alkyl group, a $C_{1-5}$ alkoxy-$C_{1-5}$ alkyl group, a $C_{2-4}$ alkoxycarbonyl-$C_{1-5}$ alkyl group, a carboxyl-$C_{1-5}$ alkyl group, a cyano-$C_{1-5}$ alkyl group, a $C_{1-5}$ alkyl group substituted with a group represented by the formula: —$NR^7R^8$ (wherein $R^7$ and $R^8$ are the same or different, and each a hydrogen atom or a $C_{1-5}$ alkyl group, or $R^7$ and $R^8$ together with the nitrogen atom to which they are attached form a pyrrolidino group, a piperidino group, a piperazino group, a morpholino group or a thiomorpholino group), an acyl group, a group represented by the formula: —$(CH_2)_{t2}CH(NH_2)COOR^9$ (wherein $R^9$ is a hydrogen atom or a $C_{1-5}$ alkyl group, t2 is 1 or 2) or a group represented by the formula:

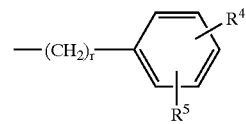

(wherein $R^4$ and $R^5$ are the same or different, and each a hydrogen atom, a hydroxyl group, a halogen atom, a $C_{1-10}$ alkyl group, a $C_{1-10}$ alkoxy group, a $C_{2-10}$ alkenyl group, a $C_{2-10}$ alkynyl group, a hydroxy-$C_{1-5}$ alkyl group, a halogeno-$C_{1-5}$ alkyl group, a $C_{1-5}$ alkoxy-$C_{1-5}$ alkyl group, a $C_{2-4}$ alkoxycarbonyl group, a carboxyl group, an acyl group, a nitro group, an amino group or an amino group which is mono- or di-substituted with $C_{1-5}$ alkyl group(s), and r is an integer of 0 to 3), $R^3$ is a hydrogen atom, a $C_{1-10}$ alkyl group, a $C_{3-10}$ cycloalkyl group, a $C_{1-5}$ alkyl-$C_{3-10}$ cycloalkyl group, a $C_{3-10}$ cycloalkyl-$C_{1-5}$ alkyl group, a $C_{2-10}$ alkenyl group or a $C_{2-10}$ alkynyl group, m is an integer of 0 to 3, n is an integer of 1 to 3, p is an integer of 0 to 5 and q is an integer of 0 to 2], a pharmaceutically acceptable salt thereof or a hydrate thereof.

Furthermore, the present invention is directed to a pharmaceutical preparation which comprises as an effective ingredient the compound represented by formula (I), the pharmaceutically acceptable salt thereof or the hydrate thereof.

In the present invention, the vinylene group refers to a cis- or a trans-vinylene group. The halogen atom refers to a fluorine atom, a chlorine atom, a bromine atom or an iodine atom.

The $C_{1-10}$ alkyl group means a straight or branched alkyl group having 1 to 10 carbon atoms, and examples of which are a methyl group, an ethyl group, a propyl group, an isopropyl group, a butyl group, an isobutyl group, a tert-butyl group, a pentyl group, a 2-ethylpropyl group, a hexyl group, an octyl group and a decanyl group.

The $C_{1-10}$ alkoxy group means a straight or branched alkoxy group having 1 to 10 carbon atoms, and examples of which are a methoxy group, an ethoxy group, a propoxy group, an isopropoxy group, a butoxy group, an isobutoxy group a tert-butoxy group, a pentyloxy group and an octyloxy group.

The $C_{2-10}$ alkenyl group means a straight or branched alkenyl group having 2 to 10 carbon atoms, and examples of which are a vinyl group, an allyl group, a 3-pentenyl group, a 4-hexenyl group, a 5-heptenyl group, a 4-methyl-3-pentenyl group, a 2,4-dimethylpentenyl group, a 6-methyl-5-heptenyl group and a 2,6-dimethyl-5-heptenyl group.

The $C_{2-10}$ alkynyl group means a straight or branched alkynyl group having 2 to 10 carbon atoms, examples of which are an ethynyl group, a propargyl group, a 3-pentynyl group, a 4-hexynyl group, a 5-heptynyl group, a 4-methyl-3-pentynyl group, a 2,4-dimethylpentynyl group, a 6-methyl-5-heptynyl group and a 2,6-dimethyl-5-heptynyl group.

The $C_{3-10}$ cycloalkyl group means a cycloalkyl group having 3 to 10 carbon atoms, examples of which are a cyclopropyl group, a cyclobutyl group, a cyclopentyl group, a cyclohexyl group and a cycloheptyl group.

The $C_{1-5}$ alkyl-$C_{3-10}$ cycloalkyl group means a cycloalkyl group having 3 to 10 carbon atoms substituted with a straight or branched alkyl group having 1 to 5 carbon atoms, examples of which are a methylcyclopropyl group, a methylcyclohexyl group and an ethylcyclohexyl group.

The $C_{3-10}$ cycloalkyl-$C_{1-5}$ alkyl group means a straight or branched alkyl group having 1 to 5 carbon atoms substituted with a cycloalkyl group having 3 to 10 carbon atoms, examples of which are a cyclopropylmethyl group, a cyclobutylmethyl group, a cyclopentylmethyl group, a cyclopentylethyl group, a cyclohexylmethyl group, a cyclohexylethyl group and a cycloheptylmethyl group.

The hydroxy-$C_{1-5}$ alkyl group means a straight or branched alkyl group having 1 to 5 carbon atoms substituted with a hydroxyl group, examples of which are a hydroxymethyl group, a hydroxyethyl group, a 2-hydroxypropyl group, a 3-hydroxypropyl group, a 4-hydroxybutyl group and a 5-hydroxypentyl group.

The halogeno-$C_{1-5}$ alkyl group means a straight or branched alkyl group having 1 to 5 carbon atoms substituted with at least one of a fluorine atom, a chlorine atom and a bromine atom, examples of which are a chloroethyl group, a 2-bromopropyl group, a 3-chloropropyl group, a 4-fluorobutyl group, a 5-chloropentyl group and a trifluoromethyl group.

The $C_{1-5}$ alkoxy-$C_{1-5}$ alkyl group means a straight or branched alkyl group having 1 to 5 carbon atoms substituted with a straight or branched alkoxy group having 1 to 5 carbon atoms, examples of which are an ethoxymethyl group, a methoxyethyl group, a 2-ethoxypropyl group, a 3-methoxypropyl group and a tert-butoxyethyl group.

The $C_{2-4}$ alkoxycarbonyl-$C_{1-5}$ alkyl group means a straight or branched $C_{1-5}$ alkyl group substituted with a straight or branched $C_{2-4}$ alkoxycarbonyl group, examples of which are a methoxycarbonylmethyl group, an ethoxycarbonylmethyl group, a 1-ethoxycarbonylethyl group and a 3-methoxycarbonylpropyl group.

The carboxyl-$C_{1-5}$ alkyl group means a straight or branched alkyl group having 1 to 5 carbon atoms substituted with a carboxyl group, examples of which are a carboxylmethyl group, a 1-carboxylethyl group, a 2-carboxylethyl group and a 3-carboxylpropyl group.

The cyano-$C_{1-5}$ alkyl group means a straight or branched alkyl group having 1 to 5 carbon atoms substituted with a cyano group, examples of which are a cyanomethyl group, a 2-cyanoethyl group, a 2-cyanopropyl group and a 3-cyanopropyl group.

Examples of the $C_{1-5}$ alkyl group substituted with a group represented by the formula: —$NR^7R^8$ are a 2-aminoethyl group, a 3-aminopropyl group, a 2-N,N-dimethylaminoethyl group, a 3-N,N-diethylaminopropyl group and a 2-piperidinoethyl group.

The acyl group includes both of an aliphatic and aromatic acyl group, and the aliphatic acyl group includes a $C_{2-10}$ alkanoyl group, a $C_{2-10}$ alkenoyl group and a $C_{3-10}$ cycloalkenoyl group, and the aromatic acyl group includes an acyl group having a benzene ring which is unsubstituted or substituted with hydroxyl group(s) or halogen atom(s), examples of which are an acetyl group, a propionyl group, an isobutyryl group, a pivaloyl group, a propioloyl group, crotonyl group, a benzoyl group, a nicotinoyl group and a cyclohexylcarbonyl group.

Examples of the pharmaceutically acceptable salt are salts with alkali metals (e.g., sodium or potassium), alkali earth metals (e.g., calcium or magnesium), ammonia, methylamine, dimethylamine, cyclopentylamine, benzylamine, piperidine, monoethanolamine, diethanolamine, monomethylmonoethanolamine, tromethamine, lysine, a tetraalkyl ammonium or tris(hydroxymethyl)aminomethane.

In the present invention, a preferable group as defined for X is $CH_2$ and a group represented by the formula: $S(O)_{q1}$ (wherein q1 is as defined above), and a more preferable group is $CH_2$.

A preferable group as defined for Y is an ethylene group, a vinylene group, an ethynylene group, a group represented by the formula: $O(CH_2)_{t1}$ or $S(O)_{q2}(CH_2)_{t1}$ (wherein q2 and t1 are as defined above), and a more preferable group is an ethylene group, a vinylene group, $OCH_2$ or $SCH_2$.

A preferable group as defined for Z is a vinylene group or a ethynylene group.

A preferable group as defined for $R^1$ is a hydrogen atom or a $C_{1-10}$ alkyl group.

A preferable group as defined for $R^2$ is a $C_{1-10}$ alkyl group, a hydroxy-$C_{1-5}$ alkyl group, a $C_{1-5}$ alkoxy-$C_{1-5}$ alkyl group, a $C_{2-4}$ alkoxycarbonyl-$C_{1-5}$ alkyl group, a cyano-$C_{1-5}$ alkyl group, a $C_{1-5}$ alkyl group substituted with a group represented by the formula: —$NR^{77}R^{88}$ (wherein $R^{77}$ and $R^{88}$ are the same or different, and each a hydrogen atom or a $C_{1-5}$ alkyl group), an acyl group, a group represented by the formula: —$(CH_2)_{t2}CH(NH_2)COOR^9$ (wherein $R^9$ and t2 are as defined above) or a group represented by the formula:

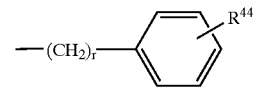

(wherein $R^{44}$ is a hydrogen atom, a halogen atom, a $C_{1-10}$ alkyl group, a $C_{1-10}$ alkoxy group, a nitro group or an amino group, and r is an integer of 0 to 3), and more preferable groups are a hydroxy-$C_{1-5}$ alkyl group, a $C_{2-4}$ alkoxycarbonyl-$C_{1-5}$ alkyl group, a $C_{1-5}$ alkyl group substituted with a di-$C_{1-5}$ alkylamino group, a $C_{2-10}$ alkanoyl group, a group represented by the formula: —$(CH_2)_{t2}CH(NH_2)COOR^9$ (wherein $R^9$ and t2 are as defined above) and a group represented by the formula:

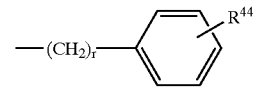

(wherein $R^{44}$ is as defined above).

A preferable group as defined for $R^3$ is a hydrogen atom, a $C_{1-10}$ alkyl group, a $C_{3-10}$ cycloalkyl group, a $C_{3-10}$ cycloalkyl-$C_{1-5}$ alkyl group or a $C_{2-10}$ alkenyl group, and a more preferable group is a hydrogen atom or a $C_{1-10}$ alkyl group.

The compounds of Formula (I) can be prepared, for example, by the methods summarized by the following reaction scheme.

In the reaction scheme, TBS is a tert-butyldimethylsilyl group, Z' is an ethylene group or a vinylene group, Et is an ethyl group, $R^6$ is a straight or branched $C_{1-10}$ alkyl group or a $C_{3-10}$ cycloalkyl group, q3 is 1 or 2, and X, Y, Z, $R^2$, $R^3$, m, n and p are as defined above.

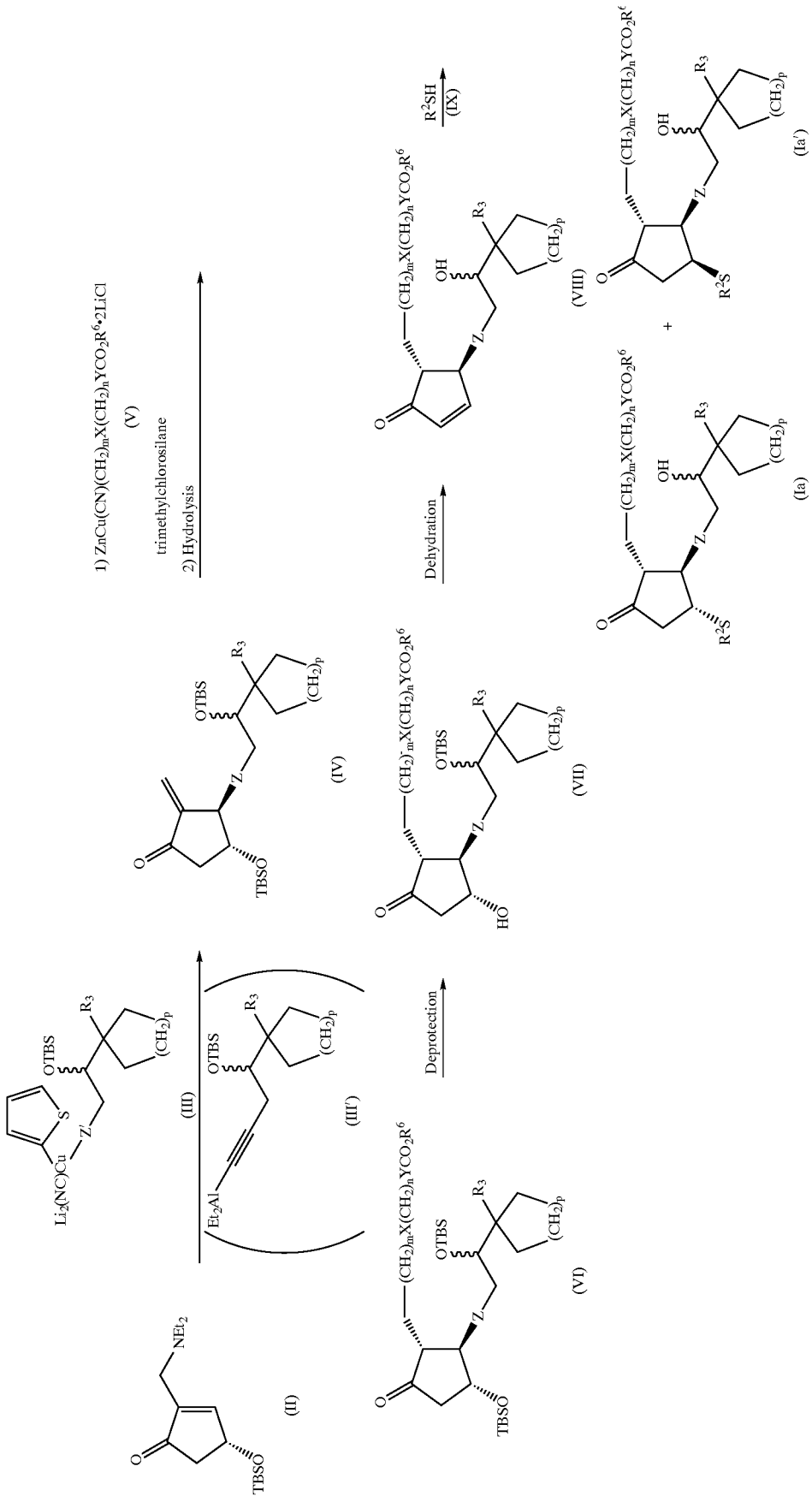

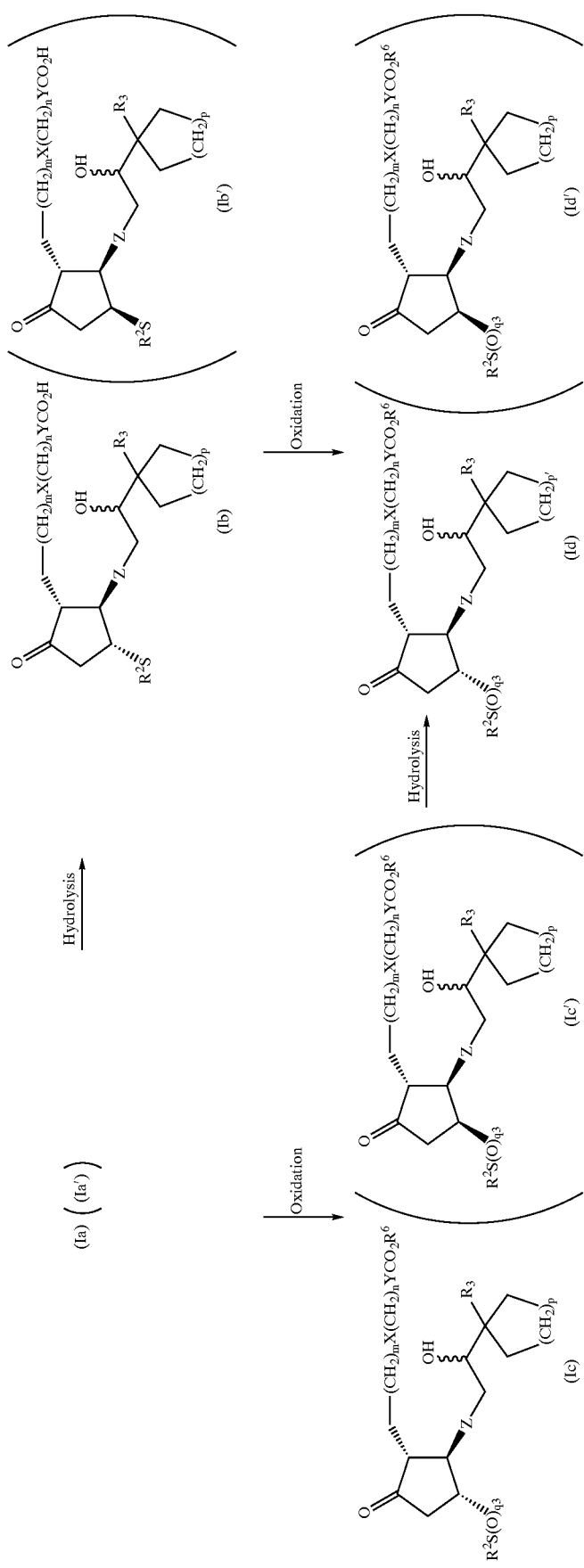

The above-mentioned reaction scheme is illustrated as follows:

(1) At first, a known compound of Formula (II) is reacted with 0.8 to 2.0 equivalents of an organic aluminum compound represented by Formula (III) or (III') in an inert solvent (e.g., benzene, toluene, tetrahydrofuran, diethyl ether, methylene chloride or n-hexane) at −78 to 30° C. according to the method of Sato et al. (*Journal of Organic Chemistry,* vol. 53, page 5590 (1988)) to stereospecifically give a compound of Formula (IV). Herein, the compound wherein Z is an ethylene group or a vinylene group (i.e., the compound wherein Z is Z' ) can be obtained by a reaction using a compound of Formula (III) at −78 to 0° C., and the compound wherein Z is an ethynylene group can be obtained by a reaction using a compound of Formula (III') at 0 to 30° C. The compound represented by Formula (III) or (III') can be prepared using a compound obtained according to the method of Skotnicki et al., in *J. Med. Chem.,* vol. 20, page 1042 (1977).

(2) The compound of Formula (IV) is reacted with 0.5 to 4 equivalents of an organic copper compound represented by Formula (V) and 0.5 to 4 equivalents of trimethylchlorosilane in an inert solvent (e.g., benzene, toluene, tetrahydrofuran, diethyl ether, methylene chloride, n-hexane or n-pentane) at −78 to 40° C., followed by hydrolysis using an inorganic acid (e.g., hydrochloric acid, sulfuric acid or nitric acid), an organic acid (e.g., acetic acid or p-toluenesulfonic acid) or an amine salt thereof (e.g., pyridinium p-toluenesulfonate) in an organic solvent (e.g., acetone, methanol, ethanol, isopropanol, diethyl ether or a mixture thereof) at 0 to 40° C. to stereoselectively give a compound of Formula (VI).

(3) The tert-butyldimethylsilyl group of the compound of Formula (VI) is removed using hydrofluoric acid, pyridinium poly(hydrogenfluoride) or hydrochloric acid in methanol, ethanol, acetonitrile, a mixture thereof or a mixture of these solvents and water under conventional conditions to give a compound of Formula (VII).

(4) The compound of Formula (VII) is subjected to dehydration using an organic acid (e.g., formic acid or acetic acid) or an inorganic acid (e.g., sulfuric acid or hydrochloric acid) in an organic solvent (e.g., methanol, ethanol, ethyl acetate or dioxane), water or a mixture thereof at 0 to 60° C. to give a compound of Formula (VIII).

(5) The compound of Formula (VIII) is reacted with 1 to 5 equivalents of a compound represented by Formula (IX) and, if necessary, an amine (e.g., triethylamine or diisobutylamine) or 0.05 to 2 equivalents of a radical generating agent (e.g., azobisisobutyronitrile, azobiscyclohexanecarbonitrile, benzoyl peroxide or triethyl borane) in an inert solvent (e.g., chloroform, benzene, toluene, xylene, n-hexane, n-pentane or acetone) at −78 to 100° C. to give PG derivatives of formulae (Ia) and (Ia') of the present invention, which are stereroisomerically different from each other at the 11-position. These compounds of formulae (Ia) and (Ia') can be purified according to a conventional separation procedure such as column chromatography.

(6) The compound of Formula (Ia) or (Ia') is hydrolyzed by a reaction with an enzyme in a buffer solution such as phosphate buffer or tris-hydrochloride buffer, if necessary, by using an organic solvent (e.g. a water-miscible solvent such as acetone, methanol or ethanol) to give a PG derivative of Formula (Ib) or (Ib').

Examples of the enzyme to be used are enzymes produced by microorganisms (e.g. enzymes produced by microorganisms belonging to Candida sp. or Pseudomonas sp.) and enzymes prepared from animal organs (e.g. enzymes prepared from pig liver or pig pancreas). Commercially available enzymes are, for example, lipase VII (derived from microorganism of Candida sp.; Sigma Co.), lipase AY (derived from microorganism of Candida sp.; Amano Pharmaceutical Co.), lipase PS (derived from microorganism of Pseudomonas sp.; Amano Pharmaceutical Co.), lipase MF (derived from microorganism of Pseudomonas sp.; Amano Pharmaceutical Co.), PLE (prepared from pig liver: Sigma Co.), lipase II (prepared from pig pancreas; Sigma Co.) or lipoprotein lipase (prepared from pig pancreas: Tokyo Kasei Kogyo Co.).

The amount of the enzyme to be used, while depending on the potency of the enzyme and the amount of the substrate (the compound of Formula (Ia)), is usually 0.1 to 20 parts by weight based on the substrate, and the reaction temperature is from 25 to 50° C., preferably 30 to 40° C.

(7) The compound of Formula (Ia) or (Ia') is oxidized using an oxidant such as sodium metaperiodate, hydrogen peroxide, peracetic acid, m-chloroperbenzoic acid or tert-butyl hydroxyperoxide in diethyl ether, methanol, ethanol, methylene chloride, water or a mixture thereof at −20 to 50° C. to give a PG derivative of Formula (Ic) or (Ic').

(8) The compound of Formula (Ic) or (Ic') is hydrolyzed using an enzyme in the similar manner as described in the above (6) to give a PG derivative of Formula (Id) or (Id'). In addition, oxidation using the compound of Formula (Ib) or (Ib') in the similar manner as described in the above (7) gives a PG derivative of Formula (Id) or (Id').

Representative compounds of the present invention are shown as follows.

| Compound | X | Y | Z | m | n | p | q | $R^1$ | $R^2$ | $R^3$ | 11-position | 16-OH |
|---|---|---|---|---|---|---|---|---|---|---|---|---|
| 1 | $CH_2$ | $CH_2CH_2$ | $CH_2CH_2$ | 2 | 0 | 1 | 0 | Me | $HO(CH_2)_2$ | nPr | α | β |
| 2 | $CH_2$ | $CH_2CH_2$ | $CH_2CH_2$ | 2 | 0 | 1 | 0 | Me | $HO(CH_2)_2$ | nPr | β | β |
| 3 | $CH_2$ | $CH_2CH_2$ | $CH_2CH_2$ | 2 | 0 | 1 | 0 | H | $HO(CH_2)_2$ | nPr | α | β |
| 4 | $CH_2$ | $CH_2CH_2$ | $CH_2CH_2$ | 2 | 0 | 2 | 0 | Me | $HO(CH_2)_2$ | cHex | α | β |
| 5 | $CH_2$ | $CH_2CH_2$ | $CH_2CH_2$ | 2 | 0 | 2 | 0 | Me | $HO(CH_2)_2$ | cHex | β | β |
| 6 | $CH_2$ | $CH_2CH_2$ | $CH_2CH_2$ | 2 | 0 | 2 | 0 | H | $HO(CH_2)_2$ | cHex | α | β |
| 7 | $CH_2$ | (E)CH=CH | $CH_2CH_2$ | 3 | 0 | 1 | 0 | Me | $HO(CH_2)_2$ | nPr | α | β |
| 8 | $CH_2$ | (E)CH=CH | $CH_2CH_2$ | 3 | 0 | 1 | 0 | Me | $HO(CH_2)_2$ | nPr | β | β |
| 9 | $CH_2$ | (E)CH=CH | $CH_2CH_2$ | 3 | 0 | 1 | 0 | H | $HO(CH_2)_2$ | nPr | α | β |
| 10 | $CH_2$ | $CH_2CH_2$ | $CH_2CH_2$ | 2 | 0 | 1 | 0 | Me | $NC(CH_2)_2$ | nPr | α | β |
| 11 | $CH_2$ | $CH_2CH_2$ | $CH_2CH_2$ | 2 | 0 | 1 | 0 | Me | $NC(CH_2)_2$ | nPr | β | β |
| 12 | $CH_2$ | $CH_2CH_2$ | $CH_2CH_2$ | 2 | 0 | 1 | 0 | H | $NC(CH_2)_2$ | nPr | α | β |

-continued

| Compound | X | Y | Z | m | n | p | q | R$^1$ | R$^2$ | R$^3$ | 11-position | 16-OH |
|---|---|---|---|---|---|---|---|---|---|---|---|---|
| 13 | CH$_2$ | CH$_2$CH$_2$ | (E)CH=CH | 3 | 0 | 1 | 0 | Me | HO(CH$_2$)$_2$ | H | α | β |
| 14 | CH$_2$ | CH$_2$CH$_2$ | (E)CH=CH | 3 | 0 | 1 | 0 | Me | HO(CH$_2$)$_2$ | H | β | β |
| 15 | CH$_2$ | CH$_2$CH$_2$ | (E)CH=CH | 3 | 0 | 1 | 0 | H | HO(CH$_2$)$_2$ | H | α | β |
| 16 | CH$_2$ | CH$_2$CH$_2$ | (E)CH=CH | 2 | 0 | 1 | 0 | Me | HO(CH$_2$)$_2$ | Me | α | β |
| 17 | CH$_2$ | CH$_2$CH$_2$ | (E)CH=CH | 2 | 0 | 1 | 0 | Me | HO(CH$_2$)$_2$ | Me | β | β |
| 18 | CH$_2$ | CH$_2$CH$_2$ | (E)CH=CH | 2 | 0 | 1 | 0 | H | HO(CH$_2$)$_2$ | Me | α | β |
| 19 | CH$_2$ | CH$_2$CH$_2$ | (E)CH=CH | 2 | 0 | 1 | 0 | Me | HO(CH$_2$)$_2$ | nPr | α | β |
| 20 | CH$_2$ | CH$_2$CH$_2$ | (E)CH=CH | 2 | 0 | 1 | 0 | Me | HO(CH$_2$)$_2$ | nPr | β | β |
| 21 | CH$_2$ | CH$_2$CH$_2$ | (E)CH=CH | 2 | 0 | 1 | 0 | H | HO(CH$_2$)$_2$ | nPr | α | β |
| 22 | CH$_2$ | CH$_2$CH$_2$ | (E)CH=CH | 2 | 0 | 1 | 0 | Me | HO(CH$_2$)$_2$ | nPr | α | α |
| 23 | CH$_2$ | CH$_2$CH$_2$ | (E)CH=CH | 2 | 0 | 1 | 0 | Me | HO(CH$_2$)$_2$ | nPr | β | α |
| 24 | CH$_2$ | CH$_2$CH$_2$ | (E)CH=CH | 2 | 0 | 1 | 0 | H | HO(CH$_2$)$_2$ | nPr | α | α |
| 25 | CH$_2$ | CH$_2$CH$_2$ | (E)CH=CH | 2 | 0 | 1 | 0 | H | HO(CH$_2$)$_2$ | nPr | β | α |
| 26 | CH$_2$ | (Z)CH=CH | (E)CH=CH | 2 | 0 | 1 | 0 | Me | HO(CH$_2$)$_2$ | nPr | α | β |
| 27 | CH$_2$ | (Z)CH=CH | (E)CH=CH | 2 | 0 | 1 | 0 | Me | HO(CH$_2$)$_2$ | nPr | β | β |
| 28 | CH$_2$ | (Z)CH=CH | (E)CH=CH | 2 | 0 | 1 | 0 | H | HO(CH$_2$)$_2$ | nPr | α | β |
| 29 | CH$_2$ | (E)CH=CH | (E)CH=CH | 2 | 0 | 1 | 0 | Me | HO(CH$_2$)$_2$ | nPr | α | β |
| 30 | CH$_2$ | (E)CH=CH | (E)CH=CH | 2 | 0 | 1 | 0 | Me | HO(CH$_2$)$_2$ | nPr | β | β |
| 31 | CH$_2$ | (E)CH=CH | (E)CH=CH | 2 | 0 | 1 | 0 | H | HO(CH$_2$)$_2$ | nPr | α | β |
| 32 | CH$_2$ | (E)CH=CH | (E)CH=CH | 2 | 0 | 1 | 0 | Me | HO(CH$_2$)$_2$ | nPr | α | α |
| 33 | CH$_2$ | (E)CH=CH | (E)CH=CH | 2 | 0 | 1 | 0 | Me | HO(CH$_2$)$_2$ | nPr | β | α |
| 34 | CH$_2$ | (E)CH=CH | (E)CH=CH | 2 | 0 | 1 | 0 | H | HO(CH$_2$)$_2$ | nPr | α | α |
| 35 | CH$_2$ | C≡C | (E)CH=CH | 2 | 0 | 1 | 0 | Me | HO(CH$_2$)$_2$ | nPr | α | β |
| 36 | CH$_2$ | C≡C | (E)CH=CH | 2 | 0 | 1 | 0 | Me | HO(CH$_2$)$_2$ | nPr | β | β |
| 37 | CH$_2$ | C≡C | (E)CH=CH | 2 | C | 1 | 0 | H | HO(CH$_2$)$_2$ | nPr | α | β |
| 38 | CH$_2$ | C≡C | (E)CH=CH | 2 | 0 | 1 | 0 | Me | HC(CH$_2$)$_2$ | nPr | α | α |
| 39 | CH$_2$ | C≡C | (E)CH=CH | 2 | 0 | 1 | 0 | Me | HO(CH$_2$)$_2$ | nPr | β | α |
| 40 | CH$_2$ | C≡C | (E)CH=CH | 2 | 0 | 1 | 0 | H | HO(CH$_2$)$_2$ | nPr | α | α |
| 41 | CH$_2$ | CH$_2$CH$_2$ | (E)CH=CH | 2 | 0 | 1 | 0 | Me | HO(CH$_2$)$_3$ | nPr | α | α |
| 42 | CH$_2$ | CH$_2$CH$_2$ | (E)CH=CH | 2 | 0 | 1 | 0 | Me | HO(CH$_2$)$_3$ | nPr | β | α |
| 43 | CH$_2$ | CH$_2$CH$_2$ | (E)CH=CH | 2 | 0 | 1 | 0 | H | HO(CH$_2$)$_3$ | nPr | α | α |
| 44 | CH$_2$ | CH$_2$CH$_2$ | (E)CH=CH | 2 | 0 | 1 | 0 | iPr | HO(CH$_2$)$_3$ | nPr | α | α |
| 45 | CH$_2$ | CH$_2$CH$_2$ | (E)CH=CH | 2 | 0 | 1 | 0 | Me | MeO$_2$CCH$_2$ | nPr | α | α |
| 46 | CH$_2$ | CH$_2$CH$_2$ | (E)CH=CH | 2 | 0 | 1 | 0 | Me | MeO$_2$CCH$_2$ | nPr | β | α |
| 47 | CH$_2$ | CH$_2$CH$_2$ | (E)CH=CH | 2 | 0 | 1 | 0 | Me | HO$_2$CCH$_2$ | nPr | α | α |
| 48 | CH$_2$ | CH$_2$CH$_2$ | (E)CH=CH | 2 | 0 | 1 | 0 | Me | Et$_2$N(CH$_2$)$_2$ | nPr | αβ | α |
| 49 | CH$_2$ | CH$_2$CH$_2$ | (E)CH=CH | 2 | 0 | 1 | 0 | cHex | nPr | nPr | α | α |
| 50 | CH$_2$ | CH$_2$CH$_2$ | (E)CH=CH | 2 | 0 | 1 | 0 | Me | nPr | nPr | α | α |
| 51 | CH$_2$ | CH$_2$CH$_2$ | (E)CH=CH | 2 | 0 | 1 | 0 | Me | nPr | nPr | β | α |
| 52 | CH$_2$ | CH$_2$CH$_2$ | (E)CH=CH | 2 | 0 | 1 | 0 | H | nPr | nPr | α | α |
| 53 | CH$_2$ | CH$_2$CH$_2$ | (E)CH=CH | 2 | 0 | 1 | 0 | Me | CH$_3$CO | nPr | αβ | α |
| 54 | CH$_2$ | CH$_2$CH$_2$ | (E)CH=CH | 2 | 0 | 1 | 0 | Me | Cys(OMe) | nPr | α | α |
| 55 | CH$_2$ | CH$_2$CH$_2$ | (E)CH=CH | 2 | 0 | 1 | 0 | Me | Cys(OMe) | nPr | β | α |
| 56 | CH$_2$ | CH$_2$CH$_2$ | (E)CH=CH | 2 | 0 | 1 | 0 | Me | m-NO$_2$Ph | nPr | α | α |
| 57 | CH$_2$ | CH$_2$CH$_2$ | (E)CH=CH | 2 | 0 | 1 | 0 | Me | p-MeOBn | nPr | α | α |
| 58 | CH$_2$ | CH$_2$CH$_2$ | (E)CH=CH | 2 | 0 | 1 | 0 | Me | p-MeOBn | nPr | β | α |
| 59 | CH$_2$ | CH$_2$CH$_2$ | (E)CH=CH | 2 | 0 | 1 | 0 | H | p-MeOBn | nPr | α | α |
| 60 | CH$_2$ | CH$_2$CH$_2$ | (E)CH=CH | 2 | 0 | 1 | 0 | Me | p-ClPh | nPr | α | α |
| 61 | CH$_2$ | CH$_2$CH$_2$ | (E)CH=CH | 2 | 0 | 1 | 0 | H | p-ClPh | nPr | α | α |
| 62 | CH$_2$ | CH$_2$CH$_2$ | (E)CH=CH | 2 | 0 | 1 | 0 | Me | HO(CH$_2$)$_2$ | cPrCH$_2$ | α | β |
| 63 | CH$_2$ | CH$_2$CH$_2$ | (E)CH=CM | 2 | 0 | 1 | 0 | H | HO(CH$_2$)$_2$ | cPrCH$_2$ | α | β |
| 64 | CH$_2$ | OCH$_2$ | (E)CH=CH | 2 | 0 | 1 | 0 | Me | HO(CH$_2$)$_2$ | nPr | α | β |
| 65 | CH$_2$ | OCH$_2$ | (E)CH=CH | 2 | 0 | 1 | 0 | Me | HO(CH$_2$)$_2$ | nPr | β | β |
| 66 | CH$_2$ | OCH$_2$ | (E)CH=CH | 2 | 0 | 1 | 0 | H | HO(CH$_2$)$_2$ | nPr | α | β |
| 67 | CH$_2$ | OCH$_2$ | (E)CH=CH | 2 | 0 | 1 | 0 | He | HO(CH$_2$)$_2$ | nPr | α | α |
| 68 | CH$_2$ | OCH$_2$ | (E)CH=CH | 2 | 0 | 1 | 0 | Me | HO(CH$_2$)$_2$ | nPr | β | α |
| 69 | CH$_2$ | OCH$_2$ | (E)CH=CH | 2 | 0 | 1 | 0 | H | HO(CH$_2$)$_2$ | nPr | α | α |
| 70 | CH$_2$ | OCH$_2$ | (E)CH=CH | 2 | 0 | 2 | 0 | Me | HO(CH$_2$)$_2$ | nPr | α | α |
| 71 | CH$_2$ | OCH$_2$ | (E)CH=CH | 2 | 0 | 2 | 0 | Me | HO(CH$_2$)$_2$ | nPr | β | α |
| 72 | CH$_2$ | OCH$_2$ | (E)CH=CH | 2 | 0 | 2 | 0 | H | HO(CH$_2$)$_2$ | nPr | α | α |
| 73 | CH$_2$ | OCH$_2$ | (E)CH=CH | 2 | 0 | 2 | 0 | Me | HO(CH$_2$)$_2$ | nPr | α | β |
| 74 | CH$_2$ | OCH$_2$ | (E)CH=CH | 2 | 0 | 2 | 0 | Me | HO(CH$_2$)$_2$ | nPr | β | β |
| 75 | CH$_2$ | OCH$_2$ | (E)CH=CH | 2 | 0 | 2 | 0 | H | HO(CH$_2$)$_2$ | nPr | α | β |
| 76 | CH$_2$ | OCH$_2$ | (E)CH=CH | 1 | 1 | 3 | 0 | Me | HO(CH$_2$)$_2$ | nPr | α | β |
| 77 | CH$_2$ | OCH$_2$ | (E)CH=CH | 1 | 1 | 3 | 0 | Me | HO(CH$_2$)$_2$ | nPr | β | β |
| 78 | CH$_2$ | OCH$_2$ | (E)CH=CH | 1 | 1 | 3 | 0 | H | HO(CH$_2$)$_2$ | nPr | α | β |
| 79 | CH$_2$ | SCH$_2$ | (E)CH=CH | 2 | 0 | 1 | 0 | Me | HO(CH$_2$)$_2$ | nPr | α | β |
| 80 | CH$_2$ | SCH$_2$ | (E)CH=CH | 2 | 0 | 1 | 0 | Me | HO(CH$_2$)$_2$ | nPr | β | β |
| 81 | CH$_2$ | SCH$_2$ | (E)CH=CH | 2 | 0 | 1 | 0 | H | HO(CH$_2$)$_2$ | nPr | α | β |
| 82 | CH$_2$ | SCH$_2$ | (E)CH=CH | 2 | 0 | 1 | 0 | Me | HO(CH$_2$)$_2$ | nPr | α | α |
| 83 | CH$_2$ | SCH$_2$ | (E)CH=CH | 2 | 0 | 1 | 0 | Me | HO(CH$_2$)$_2$ | nPr | β | α |
| 84 | CH$_2$ | SCH$_2$ | (E)CH=CH | 2 | 0 | 1 | 0 | H | HO(CH$_2$)$_2$ | nPr | α | α |
| 85 | CH$_2$ | CH$_2$CH$_2$ | C≡C | 2 | 0 | 1 | 0 | Me | HO(CH$_2$)$_2$ | nPr | α | αβ |
| 86 | CH$_2$ | CH$_2$CH$_2$ | C≡C | 2 | 0 | 1 | 0 | Me | MO(CH$_2$)$_2$ | nPr | β | αβ |
| 87 | CH$_2$ | CH$_2$CH$_2$ | C≡C | 2 | 0 | 1 | 0 | H | HO(CH$_2$)$_2$ | nPr | α | αβ |
| 88 | CH$_2$ | CH$_2$CH$_2$ | C≡C | 2 | 0 | 1 | 0 | H | HO(CH$_2$)$_2$ | nPr | β | αβ |

-continued

| Compound | X | Y | Z | m | n | p | q | $R^1$ | $R^2$ | $R^3$ | 11-position | 16-OH |
|---|---|---|---|---|---|---|---|---|---|---|---|---|
| 89 | $CH_2$ | (E)CH=CH | C≡C | 2 | 0 | 1 | 0 | Me | $HO(CH_2)_2$ | nPr | α | αβ |
| 90 | $CH_2$ | (E)CH=CH | C≡C | 2 | 0 | 1 | 0 | Me | $HO(CH_2)_2$ | nPr | β | αβ |
| 91 | $CH_2$ | (E)CH=CH | C≡C | 2 | 0 | 1 | 0 | H | $HO(CH_2)_2$ | nPr | α | αβ |
| 92 | $CH_2$ | C≡C | C≡C | 2 | 0 | 1 | 0 | Me | $HO(CH_2)_2$ | nPr | α | αβ |
| 93 | $CH_2$ | C≡C | C≡C | 2 | 0 | 1 | 0 | Me | $HO(CH_2)_2$ | nPr | β | αβ |
| 94 | $CH_2$ | C≡C | C≡C | 2 | 0 | 1 | 0 | H | $HO(CH_2)_2$ | nPr | α | αβ |
| 95 | $CH_2$ | $O(CH_2)_2$ | C≡C | 1 | 0 | 1 | 0 | Me | $HO(CH_2)_2$ | nPr | α | αβ |
| 96 | $CH_2$ | $O(CH_2)_2$ | C≡C | 1 | 0 | 1 | 0 | Me | $HO(CH_2)_2$ | nPr | β | αβ |
| 97 | $CH_2$ | $O(CH_2)_2$ | C≡C | 1 | 0 | 1 | 0 | H | $HO(CH_2)_2$ | nPr | α | αβ |
| 98 | $CH_2$ | $OCH_2$ | C≡C | 2 | 0 | 2 | 0 | Me | $HO(CH_2)_2$ | nPr | α | αβ |
| 99 | $CH_2$ | $OCH_2$ | C≡C | 2 | 0 | 2 | 0 | Me | $HO(CH_2)_2$ | nPr | β | αβ |
| 100 | $CH_2$ | $OCH_2$ | C≡C | 2 | 0 | 2 | 0 | H | $HO(CH_2)_2$ | nPr | α | αβ |
| 101 | $CH_2$ | $OCH_2$ | C≡C | 2 | 0 | 2 | 0 | Me | $MeO(CH_2)_2$ | nPr | α | αβ |
| 102 | $CH_2$ | $OCH_2$ | C≡C | 2 | 0 | 2 | 0 | Me | $MeO(CH_2)_2$ | nPr | β | αβ |
| 103 | $CH_2$ | $OCH_2$ | C≡C | 2 | 0 | 2 | 0 | H | $MeO(CH_2)_2$ | nPr | α | αβ |
| 104 | $CH_2$ | $OCH_2$ | C≡C | 2 | 0 | 2 | 0 | Me | $HO(CH_2)_2$ | $CH=CH_2$ | α | αβ |
| 105 | $CH_2$ | $OCH_2$ | C≡C | 2 | 0 | 2 | 0 | Me | $HO(CH_2)_2$ | $CH=CH_2$ | β | αβ |
| 106 | $CH_2$ | $OCH_2$ | C≡C | 2 | 0 | 2 | 0 | H | $HO(CH_2)_2$ | $CH=CH_2$ | α | αβ |
| 107 | $CH_2$ | $SCH_2$ | C≡C | 2 | 0 | 1 | 0 | Me | $HO(CH_2)_2$ | nPr | α | αβ |
| 108 | $CH_2$ | $SCH_2$ | C≡C | 2 | 0 | 1 | 0 | Me | $HO(CH_2)_2$ | nPr | β | αβ |
| 109 | S | $CH_2CH_2$ | C≡C | 0 | 2 | 1 | 0 | H | $HO(CH_2)_2$ | nPr | α | αβ |
| 110 | S | $CH_2CH_2$ | C≡C | 0 | 2 | 1 | 0 | H | $HO(CH_2)_3$ | nPr | α | αβ |
| 111 | S | $CH_2CH_2$ | $CH_2CH_2$ | 0 | 3 | 1 | 0 | Me | $HO(CH_2)_2$ | nPr | α | α |
| 112 | S | $CH_2CH_2$ | $CH_2CH_2$ | 0 | 3 | 1 | 0 | H | $HO(CH_2)_2$ | nPr | α | β |
| 113 | S | $CH_2CH_2$ | $CH_2CH_2$ | 0 | 3 | 2 | 0 | Me | $HO(CH_2)_2$ | cHex | α | β |
| 114 | S | (E)CH=CH | $CH_2CH_2$ | 0 | 2 | 1 | 0 | tBu | $HO(CH_2)_2$ | nPr | α | β |
| 115 | S | (E)CH=CH | $CH_2CH_2$ | 0 | 2 | 1 | 0 | Me | $HO(CH_2)_2$ | nPr | α | β |
| 116 | S | $CH_2CH_2$ | (E)CH=CH | 0 | 3 | 1 | 0 | Me | $HO(CH_2)_2$ | H | α | β |
| 117 | S | $CH_2CH_2$ | (E)CH=CH | 0 | 3 | 1 | 0 | cHex | $HO(CH_2)_2$ | H | α | β |
| 118 | S | $CH_2CH_2$ | (E)CH=CH | 0 | 2 | 1 | 0 | Me | $HO(CH_2)_2$ | nPr | α | β |
| 119 | S | $CH_2CH_2$ | (E)CH=CH | 0 | 2 | 1 | 0 | H | $HO(CH_2)_2$ | nPr | α | β |
| 120 | S | $CH_2CH_2$ | (E)CH=CH | 0 | 2 | 1 | 0 | Me | $HO(CH_2)_2$ | nPr | α | α |
| 121 | S | $CH_2CH_2$ | (E)CH=CH | 0 | 2 | 1 | 0 | H | $HO(CH_2)_2$ | nPr | α | α |
| 122 | S | $CH_2CH_2$ | (E)CH=CH | 0 | 3 | 1 | 0 | Me | $HO(CH_2)_3$ | nPr | α | α |
| 123 | S | $CH_2CH_2$ | (E)CH=CH | 0 | 3 | 1 | 0 | H | $HO(CH_2)_3$ | nPr | α | α |
| 124 | S | (Z)CH=CH | $CH_2CH_2$ | 0 | 2 | 1 | 0 | H | $HO(CH_2)_2$ | nPr | α | β |
| 125 | S | (E)CH=CH | $CH_2CH_2$ | 0 | 2 | 1 | 0 | Me | $HO(CH_2)_2$ | nPr | α | α |
| 126 | S | (E)CH=CH | $CH_2CH_2$ | 0 | 2 | 1 | 0 | Me | $HO(CH_2)_2$ | nPr | β | α |
| 127 | S | C≡C | (E)CH=CH | 0 | 2 | 1 | 0 | H | $HO(CH_2)_2$ | nPr | α | β |
| 128 | S | $OCH_2$ | (E)CH=CH | 0 | 2 | 1 | 0 | Me | $HO(CH_2)_2$ | nPr | α | α |
| 129 | S | $OCH_2$ | (E)CH=CH | 0 | 2 | 1 | 0 | H | $HO(CH_2)_2$ | nPr | α | α |
| 130 | S | $OCH_2$ | (E)CH=CH | 0 | 3 | 2 | 0 | Me | $HO(CH_2)_2$ | nPr | α | β |
| 131 | S | $OCH_2$ | (E)CH=CH | 0 | 3 | 2 | 0 | Me | $HO(CH_2)_2$ | nPr | β | β |
| 132 | S | $SCH_2$ | (E)CH=CH | 0 | 2 | 1 | 0 | Me | $HO(CH_2)_2$ | nPr | α | α |
| 133 | S | $SCH_2$ | (E)CH=CH | 0 | 2 | 1 | 0 | H | $HO(CH_2)_2$ | nPr | α | α |
| 134 | S(O) | $S(O)CH_2$ | (E)CH=CH | 0 | 2 | 1 | 1 | Me | $HO(CH_2)_2$ | Me | α | αβ |
| 135 | $S(O)_2$ | $S(O)_2CH_2$ | (E)CH=CH | 0 | 2 | 1 | 2 | Me | $HO(CH_2)_2$ | Me | α | αβ |
| 136 | S | $CH_2CH_2$ | C≡C | 0 | 2 | 1 | 0 | H | $HO(CH_2)_2$ | nPr | α | αβ |
| 137 | S | $CH_2CH_2$ | C≡C | 0 | 2 | 1 | 0 | H | $HO(CH_2)_2$ | nPr | β | αβ |
| 138 | S | (E)CH=CH | C≡C | 0 | 2 | 1 | 0 | Me | $HO(CH_2)_2$ | nPr | α | αβ |
| 139 | S | (E)CH=CH | C≡C | 0 | 2 | 1 | 0 | H | $HO(CH_2)_2$ | nPr | α | αβ |
| 140 | S | C≡C | C≡C | 0 | 3 | 1 | 0 | Me | $HO(CH_2)_2$ | nPr | α | αβ |
| 141 | S | C≡C | C≡C | 0 | 3 | 1 | 0 | H | $HO(CH_2)_2$ | nPr | α | αβ |
| 142 | S | C≡C | C≡C | 0 | 2 | 1 | 0 | Me | $HO(CH_2)_2$ | nPr | α | αβ |
| 143 | S | $OCH_2$ | C≡C | 0 | 2 | 1 | 0 | H | $HO(CH_2)_2$ | nPr | α | αβ |
| 144 | S | $OCH_2$ | C≡C | 0 | 2 | 2 | 0 | H | $HO(CH_2)_2$ | nPr | α | αβ |
| 145 | S | $OCH_2$ | C≡C | 0 | 2 | 2 | 0 | Me | $HOCCH_2)_2$ | $CH=CH_2$ | α | αβ |
| 146 | S | $OCH_2$ | C≡C | 0 | 2 | 2 | 0 | H | $HO(CH_2)_2$ | $CH=CH_2$ | α | αβ |
| 147 | S | $S(CH_2)_2$ | C≡C | 0 | 2 | 1 | 0 | Me | $HO(CH_2)_2$ | nPr | α | αβ |
| 148 | S | $SCH_2$ | C≡C | 0 | 2 | 1 | 0 | Me | $HO(CH_2)_2$ | nPr | β | αβ |
| 149 | S | $SCH_2$ | C≡C | 0 | 2 | 1 | 0 | H | $HO(CH_2)_2$ | nPr | α | αβ |
| 150 | S | $O(CH_2)_2$ | C≡C | 0 | 2 | 1 | 0 | H | $HO(CH_2)_3$ | nPr | α | αβ | npr: n-propyl, iPr: isopropyl, cHex: cyclohexyl, $cPrCH_2$: cyclopropylmethyl, $m-NO_2Ph$: m-nitrophenyl, p-MeOBn: p-methoxybenzyl, p-ClPh: p-chlorophenyl, Cys-OMe: $MeO_2CCH(NH_2)CH_2$, 11: position: binding of the $R^2$ group to the cyclopentane ring, 16 position: binding of the carbon atom and the hydroxyl group at the 16-position. (E)CH═CH: trans-vinylene, (Z)CH═CH: cis-vinylene.

The compounds of the present invention can be administered systemically or topically; orally or parenterally such as rectally, subcutaneously, intramuscularly or intravenously, and preferably orally or intravenously. For example, the dosage form for oral administration includes tablets, powders, granules, dusting powders, capsules, solutions, emulsions or suspensions, each of which can be prepared according to conventional methods. The dosage form for intravenous administration includes aqueous or non-aqueous solutions, emulsions, suspensions or solid preparations to be dissolved in a solvent for injection immediately before use. Furthermore, the compounds of the present invention can be formulated into the form of inclusion compounds with α-, β- or γ-cyclodextrin, or methylated cyclodextrin. In addition, the compounds of the present invention can be administered by injection in the form of aqueous or non-aqueous solutions, emulsions, suspensions, etc. The dose is varied by the age, body weight, etc., but it is generally from 1 ng to 1 mg/day per adult, which can be administered in a single dose or divided doses.

BEST MODE FOR CARRYING OUT THE INVENTION

The present invention is illustrated in more details by the following examples and experiment, but it is not limited by these descriptions.

EXAMPLE 1

(11R,16R)-11,15-Dideoxy-11-(2-hydroxyethylthio)-16-hydroxy-17,17-trimethylene-$PGE_1$ methyl ester (Compound 19) and (11S,16R)-11,15-dideoxy-11-(2-hydroxyethylthio)-16-hydroxy-17,17-trimethylene-$PGE_1$, methyl ester (Compound 20)

(1) To a diethyl ether solution (117 ml) of (1E,4RS)-1-iodo-4-(tert-butyldimethylsiloxy)-5,5-trimethylene-1-octene (11.94 g) was added tert-butyl lithium (2.13 M, pentane solution, 27.5 ml) under an argon stream at −78° C., followed by stirring at the same temperature for 30 minutes. To the solution was added lithium 2-thienylcyanocuprate (0.25 M, tetrahydrofuran solution, 140.3 ml) at −78° C., followed by stirring at the same temperature for 20 minutes. To the solution was added dropwise (4R)-2-(N,N-diethylamino)methyl-4-(tert-butyldimethylsiloxy)cyclopent-2-en-1-one (0.25 M, diethyl ether solution, 117 ml) at −78° C., and the temperature was raised to 0C over about an hour. The reaction solution was poured into a mixture of hexane (300 ml) and a saturated aqueous ammonium chloride solution (300 ml) with stirring, the organic layer was separated, and the aqueous layer was extracted with hexane (150 ml). The resulting organic layers were combined, dried over anhydrous magnesium sulfate and filtered. The filtrate was concentrated under reduced pressure, and the resulting crude product was purified by a silica gel column chromatography (developing solvent; hexane:ethyl acetate=49:1) to give (3R,4R)-2-methylene-3-[(1E,4RS)-4-tert-butyldimethylsiloxy-5,5-trimethyleneoct-1-enyl]-4-(tert-butyldimethylsiloxy)cyclopentan-1-one (9.28 g).

$^1$H-NMR(CDCl$_3$,200 MHz) δ ppm; 0.05(s,9H),0.06(s,3H),0.70–1.10(m,3H),0.87(s,9H),0.91 and 0.92(2S,9H), 1.15–2.52(m,13H), 2.63(dd,J=17.9,6.3 Hz,1H),3.18–3.31 (m,1H),3.52–3.62(m,1H),3.98–4.12(m,1H),5.18–5.38(m, 2H),5.54–5.79(m,1H),6.07–6.13(m,1H)

IR(neat) cm$^{-1}$; 2957,2930,2897,2858,1734,1643,1472, 1362,1256,1090,1007, 972,939,837,812,776,670

(2) Under an argon stream, copper (I) cyanide-dilithium dichloride (1.0 M, tetrahydrofuran solution, 27.6 ml) was added to 5-methoxycarbonylpentyl zinc (II) iodide (0.77 M, tetrahydrofuran solution, 33.6 ml) at −70° C., followed by stirring at the same temperature for 20 minutes. To the solution were added the compound obtained in the above (1) (0.25 M, diethyl ether solution, 69.2 ml) and chlorotrimethylsilane (3.8 ml) at −70° C., and the temperature was raised to 0° C. with stirring over about 2 hours. To the reaction solution was added a saturated aqueous ammonium chloride solution, followed by extraction with hexane. The organic layer was washed with a saturated aqueous sodium bicarbonate solution and a saturated aqueous sodium chloride solution, dried over anhydrous magnesium sulfate and filtered. The filtrate was concentrated, the resulting residue was dissolved in diethyl ether (3.5 ml)-isopropyl alcohol (13.8 ml), and pyridinium p-toluenesulfonate (100 mg) was added, followed by stirring at room temperature overnight. The reaction solution, after addition of hexane (150 ml), was washed with a saturated aqueous sodium bicarbonate solution and a saturated aqueous sodium chloride solution, dried, filtered and concentrated, and the resulting crude product was purified by a silica gel column chromatography (developing solvent; hexane:ethyl acetate=49:1 to 9:1) to give (16RS)-15-deoxy-16-hydroxy-17,17-trimethylene-$PGE_1$ methyl ester 11,16-bis(tert-butyldimethylsilyl ether) (7.56 g).

$^1$H-NMR(CDCl$_3$,200 MHz) δ ppm; 0.02(s,3H),0.05(s, 3H),0.06(s,3H),0.07(s,3H),0.70–1.00(m,3H),0.89(s,9H), 0.92 and 0.93(2s,9H),1.10–2.50(m,27H),2.51–2.68(m,1H), 3.55–3.64(m,1H), 3.68(s,3H), 3.92–4.06(m,1H),5.23–5.39 (m,1H),5.53–5.74(m,1H)

IR(neat) cm$^{-1}$; 2955,2931,2857,1746,1606,1464,1436, 1361,1256,1159,1098, 1007,973,939,837,775,670

(3) To an acetonitrile solution (396 ml) of the compound obtained in (2) (7.56 g) was added 46% aqueous hydrofluoric acid solution (89 ml) at 0° C., followed by stirring at the same temperature for 3 hours. The reaction solution was poured into a mixture of ethyl acetate (2000 ml) and a saturated aqueous sodium bicarbonate solution (2670 ml) with stirring, the organic layer was separated, and the aqueous layer was extracted with ethyl acetate. The organic layers were combined, washed with a saturated aqueous sodium bicarbonate solution and a saturated aqueous sodium chloride solution, dried over anhydrous magnesium sulfate and filtered. The filtrate was concentrated under reduced pressure, and the resulting crude product was purified by a silica gel column chromatography (developing solvent; hexane:ethyl acetate=1:1) to give (16R)-15-deoxy-16-hydroxy-17,17-trimethylene-$PGE_1$ methyl ester (2.07 g) and (16S)-15-deoxy-16-hydroxy-17,17-trimethylene-$PGE_1$ methyl ester (2.15 g).

(16R)-15-Deoxy-16-hydroxy-17,17-trimethylene-$PGE_1$ methyl ester $^1$H-NMR(CDCl$_3$,300 MHz) δ ppm; 0.95(t,J=6.8 Hz,3H), 1.20–2.12(m,22H),2.16–2.42(m,4H), 2.23(dd,J=18.4,9.6 Hz,1H),2.29(t,J=7.5 Hz,2H), 2.74(ddd,J=18.4,7.5,1.2 Hz,1H),3.58(dd,J=10.0,2.4 Hz,1H), 3.66(s,3H),4.00–4.12 (m,1H),5.48(dd,J=15.3,8.5 Hz,1H), 5.75(ddd,J=15.3,7.8,6.4 Hz,1H)

IR(neat) cm$^{-1}$; 3436,2932,2859,1742,1437,1244,1167, 1075,972

(16S)-15-Deoxy-16-hydroxy-17,17-trimethylene-$PGE_1$ methyl ester $^1$H-NMR(CDCl$_3$,300 MHz) δ ppm; 0.95(t,J=6.9 Hz,3H), 1.22–2.10(m,22H),2.20–2.41(m,3H), 2.22(dd,J=18.4,9.8 Hz,1H),2.29(t,J=7.4 Hz,2H),2.62–2.86(br,1H), 2.73(ddd,J= 18.4,7.4,1.2 Hz,1H), 3.56(dd,J=10.2,2.4 Hz,1H), 3.66(s, 3H),3.98–4.08(m,1H), 5.43(dd,J=15.2,8.8 Hz,1H), 5.72 (ddd,J=15.2,8.3,5.8 Hz,1H)

IR(neat) cm$^{-1}$; 3401,2932,2859,1742,1437,1244,1168, 1074,969

(4) To an ethyl acetate solution (52 ml) of (16R)-15-deoxy-16-hydroxy-17,17-trimethylene-$PGE_1$ methyl ester (640 mg) obtained in (3) was added an ethyl acetate solution (4 M, 2.35 ml) of hydrochloric acid at room temperature, followed by stirring for 1.5 hours. The reaction solution was neutralized with a saturated aqueous sodium bicarbonate solution, and the organic layer was separated, washed with a saturated aqueous sodium chloride solution, dried over anhydrous magnesium sulfate and filtered. The filtrate was concentrated under reduced pressure, and the resulting crude product was purified by a silica gel column chromatography (developing solvent; hexane:ethyl acetate=5:1) to give (16R)-15-deoxy-16-hydroxy-17,17-trimethylene-$PGE_1$ methyl ester (447 mg).

$^1$H-NMR(CDCl$_3$,200 MHz) δ ppm; 0.94(t,J=6.9 Hz,3H), 1.25–2.38(m,23H),1.60(d,J=4.9 Hz,1H), 2.30(t,J=7.5 Hz,2H),3.15–3.30(m,1H),3.48–3.71(m,1H), 3.67(s,3H), 5.42–5.76(m,1H),5.50(dd,J=15.6,7.5 Hz,1H), 6.15(dd,J=5.7,2.0 Hz,1H), 7.49(dd,J=5.7,2.4 Hz,1H)

IR(neat) cm$^{-1}$; 3496,2930,2858,1739,1707,1587,1465, 1436,1351,1197,1174, 1068,1030,971,881,800,430

(5) To a chloroform solution (5.6 ml) of the compound obtained in (4) (438 mg) were added 2-mercaptoethanol (0.157 ml) and diisopropylamine (0.031 ml), followed by stirring at room temperature overnight. The reaction solution was applied to a short silica gel column chromatography (developing solvent; ethyl acetate), and the resulting crude product was purified by a silica gel column chromatography (developing solvent; hexane:ethyl acetate=1:1 to ethyl acetate) to give Compound 19 (293 mg) and Compound 20 (198 mg).

Compound 19:

$^1$H-NMR(CDCl$_3$,300 MHz) δ ppm; 0.95(t,J=7.1 Hz,3H), 1.21–2.45(m,26H), 2.19(dd,J=18.6,11.3 Hz,1H),2.29(t,J=7.5 Hz,2H),2.73–2.90(m,3H),2.96–3.09(m,1H),3.54–3.63 (m,1H),3.65–3.82(m,2H),3.66(s,3H),5.47(dd,J=15.2,8.6 Hz,1H),5.66–5.80(m,1H)

IR(neat) cm$^{-1}$; 3435,2930,2859,1739,1460,1436,1278, 1202,1173,1065,1046, 971,847,742,500

Compound 20:

$^1$H-NMR(CDCl$_3$,300 MHz) δ ppm; 0.94(t,J=6.9 Hz,3H),1.20–2.91(m,30H),2.29(t,J=7.5 Hz,2H), 3.53–3.63(m,2H),3.65–3.82(m,2H),3.66(s,3H), 5.61(ddd,J=15.5,7.5,5.5 Hz,1H),5.71(dd,J=15.5,7.1 Hz, 1H)

IR(neat) cm$^{-1}$; 3435,2930,2859,1739,1436,1384,1276, 1199,1169,1066,973, 772

EXAMPLE 2

(11R,16R)-11,15-Dideoxy11-(2-hydroxyethylthio)-16-hydroxy-17,17-trimethylene-$PGE_1$ (Compound 21)

To an acetone solution (2 ml) of (11R,16R)-11,15-dideoxy-11-(2-hydroxyethylthio)-16-hydroxy-17,17-trimethylene-$PGE_1$ methyl ester obtained in Example 1 (187 mg) were added water (10 ml) and phosphate buffer solution (pH=8.0, 0.2 M, 10 ml), and further PLE (produced by Sigma Co., 3.36 unit/μl, aqueous ammonium sulfate solution, 59 μl) was added, followed by stirring at room temperature for 2 days. The mixture was adjusted to pH 4 with 1 M hydrochloric acid, salted out with ammonium sulfate and extracted with ethyl acetate. The organic layer was washed with a saturated aqueous sodium chloride solution, dried over anhydrous magnesium sulfate and filtered. The filtrate was concentrated under reduced pressure, and the resulting crude product was purified by a silica gel column chromatography (developing solvent; ethyl acetate) to give the title compound (130 mg).

$^1$H-NMR(CDCl$_3$,300 MHz) δ ppm; 0.94(t,J=7.0 Hz,3H), 1.20–2.45(m,27H), 2.20(dd,J=18.5,11.2 Hz,1H),2.33(t,J=7.2 Hz,2H),2.71–2.89(m,3H),2.96–3.09(m,1H),3.62(dd,J=9.6,2.5 Hz,1H), 3.74(t,J=6.0 Hz,2H),5.46(dd,J=15.3,8.6 Hz,1H),5.66–5.80(m,1H)

IR(neat) cm$^{-1}$; 3455,2930,2859,1739,1465,1429,1402, 1278,1239,1180,1160, 1047,970,757

EXAMPLE 3

(11R,16S)-11,15-Dideoxy-11-(2-hydroxyethylthio)-16-hydroxy-17,17-trimethylene-$PGE_1$ methyl ester (Compound 22) and (11S,16S)-11,15-dideoxy-11-(2-hydroxyethylthio)-16-hydroxy-17,17-trimethylene-$PGE_1$ methyl ester (Compound 23)

(1) Following the substantially same manner as in Example 1(4) using (16S)-15-deoxy-16-hydroxy-17,17-trimethylene-$PGE_1$ methyl ester which was the compound obtained in Example 1(3) in place of (16R)-15-deoxy-16-hydroxy-17,17-trimethylene-$PGE_1$ methyl ester in Example 1(4), thereby (16S)-15-deoxy-16-hydroxy-17,17-trimethylene-$PGE_1$ methyl ester was obtained.

$^1$H-NMR(CDCl$_3$,200 MHz) δ ppm; 0.94(t,J=6.9 Hz,3H), 1.20–2.37(m,24H),2.30(t,J=7.5 Hz,2H), 3.18–3.29(m,1H), 3.48–3.61(m,1H),3.67(s,3H), 5.48(dd,J=15.2,7.9 Hz,1H), 5.68(dt,J=15.2,6.9 Hz,1H), 6.15(dd,J=5.7,2.2 Hz,1H), 7.48 (dd,J=5.7,2.4 Hz,1H)

IR(neat) cm$^{-1}$; 3468,2930,2858,1739,1707,1587,1436, 1351,1173,1069,1030, 972,881,809,504

(2) Following the substantially same manner as in Example 1(5) using the compound obtained in (1), thereby the title compounds were obtained.

Compound 22:

$^1$H-NMR(CDCl$_3$,300 MHz) δ ppm; 0.94(t,J=6.9 Hz,3H), 1.20–2.11(m,23H),2.13–2.43(m,2H), 2.20(dd,J=18.6,11.3 Hz,1H),2.29(t,J=7.5 Hz,2H),2.52–2.66(m,1H),2.71–2.90(m,3H),2.95–3.08(m,1H),3.52–3.61(m,1H),3.63–3.81(m,2H), 3.66(s,3H), 5.41(dd,J=15.0,9.3 Hz,1H),5.66(ddd,J=15.0,9.5, 5.2 Hz,1H)

IR(neat) cm$^{-1}$; 3435,2930,2859,1740,1457,1436,1401, 1364,1275,1205,1173, 1065,1048,970,847,742

Compound 23:

$^1$H-NMR(CDCl$_3$,300 MHz) δ ppm; 0.94(t,J=6.9 Hz,3H), 1.20–2.91(m,30H),2.29(t,J=7.5 Hz,2H), 3.44–3.68(m,1H), 3.53(dd,J=10.3,2.1 Hz,1H),3.66(s,3H), 3.76(t,J=5.5 Hz,2H), 5.57–5.73(m,2H)

IR(neat) cm$^{-1}$; 3436,2930,2859,1739,1436,1384,1277, 1199,1170,1066,973, 875,726

EXAMPLE 4

(11R,16S)-11,15-Dideoxy-11-(2-hydroxyethylthio)-16-hydroxy-17,17-trimethylene-$PGE_1$ (Compound 24)

Following the substantially same manner as in Example 2 using (11R,16S)-11,15-dideoxy-11-(2-hydroxyethylthio)-16-hydroxy-17,17-trimethylene-$PGE_1$ methyl ester obtained in Example 3, thereby the title compound was obtained.

$^1$H-NMR(CDCl$_3$,300 MHz) δ ppm; 0.94(t,J=6.9 Hz,3H), 1.19–2.10(m,25H), 2.20(dd,J=18.5,11.3 Hz,1H),2.23–2.44 (m,2H), 2.33(t,J=7.4 Hz,2H),2.71–2.89(m,1H), 2.80(dt,J=8.5,5.9 Hz,1H),2.96–3.08(m,1H), 3.58(dd,J=10.4,2.2 Hz,1H),3.74(t,J=5.9 Hz,2H), 5.42(dd,J=15.1,8.8 Hz,1H), 5.67(ddd,J=15.1,9.1,5.3 Hz,1H)

IR(neat) cm$^{-1}$; 3432,2930,2859,1739,1465,1402,1279, 1180,1065,970,876,757, 667

EXAMPLE 5

(11S,16S)-11,15-Dideoxy-11-(2-hydroxyethylthio)-16-hydroxy-17,17-trimethylene-PGE$_1$ (Compound 25)

Following the substantially same manner as in Example 2 using (11S,16S)-11,15-dideoxy-11-(2-hydroxyethylthio)-16-hydroxy-17,17-trimethylene-PGE$_1$ methyl ester obtained in Example 3, thereby the title compound was obtained.

$^1$H-NMR(CDCl$_3$,300 MHz) δ ppm; 0.94(t,J=6.9 Hz,3H), 1.17–2.09(m,25H),2.24–2.38(m,2H), 2.34(t,J=7.2 Hz,2H), 2.45–2.92(m,4H),3.52–3.64(m,1H), 3.55(dd,J=10.3,2.1 Hz,1H),3.76(t,J=5.8 Hz,2H),5.63–5.69(m,2H)

IR(neat) cm$^{-1}$; 3400,2930,2859,1734,1465,1401,1281, 1164,1046,1013,972, 875,805,756,666

EXAMPLE 6

(11R,16S)-11,15-Dideoxy-11-(3-hydroxypropylthio)-16-hydroxy-17,17-trimethylene-PGE$_1$ methyl ester (Compound 41) and (11S,16S)-11,15-dideoxy-11-(3-hydroxypropylthio)-16-hydroxy-17,17-trimethylene-PGE$_1$ methyl ester (Compound 42)

Following the substantially same manner as in Example 1(5) using the compound obtained in Example 3(1) and 3-mercaptopropanol in place of 2-mercaptoethanol in Example 1(5), thereby the title compounds were obtained.

Compound 41:

$^1$H-NMR(CDCl$_3$,300 MHz) δ ppm;

0.94(t,J=7.0 Hz,3H),1.22–2.46(m,28H), 2.20(dd,J=18.4, 11.2 Hz,1H),2.29(t,J=7.5 Hz,2H), 2.74(t,J=7.1 Hz,2H),2.82 (ddd,J=18.4,7.7,1.2 Hz,1H),2.91–3.04(m,1H),3.50–3.59(m, 1H),3.65–3.80(m,2H),3.66(s,3H), 5.42(dd,J=15.2,8.9 Hz,1H),5.63(ddd,J=15.2,9.6,5.1 Hz,1H)

IR(neat) cm$^{-1}$; 3454,2930,2859,1740,1734,1436,1363, 1262,1174,1065,970, 876,724

Compound 42:

$^1$H-NMR(CDCl$_3$,300 MHz) δ ppm; 0.94(t,J=6.8 Hz,3H), 1.23–2.90(m,32H),2.29(t,J=7.5 Hz,2H), 3.49–3.58(m,2H), 3.65–3.80(m,2H),3.66(s,3H),5.55–5.72(m,2H)

IR(neat) cm$^{-1}$; 3453,2930,2859,1739,1734,1436,1363, 1262,1201,1170,1066, 973

EXAMPLE 7

(11R,16S)-11,15-Dideoxy-11-(3-hydroxypropylthio)-16-hydroxy-17,17-trimethylene-PGE$_1$ (Compound 43)

Following the substantially same manner as in Example 2 using (11R,16S)-11,15-dideoxy-11-(3-hydroxypropylthio)-16-hydroxy-17,17-trimethylene-PGE$_1$ methyl ester obtained in Example 6, thereby the title compound was obtained.

$^1$H-NMR(CDCl$_3$,300 MHz) δ ppm; 0.94(t,J=6.9 Hz,3H), 1.21–2.10(m,28H), 2.20(dd,J=18.4,11.3 Hz,1H),2.23–2.44 (m,1H), 2.33(t,J=7.3 Hz,2H),2.73(t,J=7.1 Hz,2H), 2.82(ddd, J=18.4,7.8,0.9 Hz,1H),2.91–3.04(m,1H), 3.56(dd,J=10.5,2.1 Hz,1H),3.74(dt,J=0.8,6.0 Hz,2H), 5.43(dd,J=15.1,8.9 Hz,1H),5.65(ddd,J=15.1,9.3,5.4 Hz,1H)

IR(neat) cm$^{-1}$; 3432,2930,2859,1739,1465,1434,1402, 1268,1182,1065,970, 907,876,765,666

EXAMPLE 8

(11R,16S)-11,15-Dideoxy-11-methoxycarbonylmethylthio-16-hydroxy-17,17-trimethylene-PGE$_1$ methyl ester (Compound 45) and (11S,16S)-11,15-dideoxy-11-methoxycarbonylmethylthio-16-hydroxy-17,17-trimethylene-PGE$_1$ methyl ester (Compound 46)

Following the substantially same manner as in Example 1(5) using the compound obtained in Example 3(1) and methyl thioglycolate in place of 2-mercaptoethanol in Example 1(5), thereby the title compounds were obtained.

Compound 45:

$^1$H-NMR(CDCl$_3$,300 MHz) δ ppm; 0.94(t,J=6.8 Hz,3H), 1.20–2.44(m,25H), 2.19(dd,J=18.5,11.1 Hz,1H),2.29(t,J= 7.5 Hz,2H), 2.86(ddd,J=18.5,7.6,0.9 Hz,1H),3.16(dt,J=7.6, 11.1 Hz,1H), 3.29(d,J=14.8 Hz,1H),3.36(d,J=14.8 Hz,1H), 3.49–3.58(m,1H),3.66(s,3H),3.75(s,3H), 5.43(dd,J=15.2,8.7 Hz,1H), 5.65(ddd,J=15.2,9.0,5.4 Hz,1H)

IR(neat) cm$^{-1}$; 3543,2930,2858,1740,1436,1279,1159, 1009,970,876

Compound 46:

$^1$H-NMR(CDCl$_3$,300 MHz) δ ppm; 0.94(t,J=6.8 Hz,3H), 1.22–2.14(m,21H),2.11(d,J=3.4 Hz,1H), 2.23–2.35(m,2H), 2.29(t,J=7.5 Hz,2H),2.43–2.54(m,1H), 2.64(dd,J=18.7,7.2 Hz,1H),2.82–2.93(m,1H), 3.22(d,J=14.8 Hz,1H),3.34(d,J= 14.8 Hz,1H), 3.49–3.57(m,1H),3.65–3.79(m,1H),3.66(s, 3H),3.74(s,3H),5.55–5.73(m,2H)

IR(neat) cm$^{-1}$; 3543,2930,2858,1739,1436,1281,1197, 1160,1070,1010,974, 876

EXAMPLE 9

(11RS,16S)-11,15-Dideoxy-11-[2-(N,N-diethylamino)ethylthio]-16-hydroxy-17,17-trimethylene-PGE$_1$ methyl ester (Compound 48)

Following the substantially same manner as in Example 1(5) using the compound obtained in Example 3(1) and 2-(N,N-diethylamino)ethanethiol in place of 2-mercaptoethanol in Example 1(5), thereby the title compound was obtained.

$^1$H-NMR(CDCl$_3$,300 MHz) δ ppm; 0.94(t,J=6.8 Hz,3H), 1.02(t,J=7.2 Hz,6H),1.20–3.64(m,37H), 2.29(t,J=7.5 Hz,2H),3.66(s,3H),5.38–5.74(m,2H)

IR(neat) cm$^{-1}$: 3523,2930,2858,1740,1456,1436,1375, 1198,1173,1068,1030, 970,876,785,726

EXAMPLE 10

(11R,16S)-11,15-Dideoxy-11-propylthio-16-hydroxy-17,17-trimethylene-PGE$_1$ methyl ester (Compound 50) and (11S,16S)-11,15-dideoxy-11-propylthio-16-hydroxy-17,17-trimethylene-PGE$_1$ methyl ester (Compound 51)

Following the substantially same manner as in Example 1(5) using the compound obtained in Example 3(1) and 1-propanethiol in place of 2-mercaptoethanol in Example 1(5), thereby the title compounds were obtained.

Compound 50:

$^1$H-NMR(CDCl$_3$,300 MHz) δ ppm; 0.94(t,J=6.8 Hz,3H), 0.98(t,J=7.3 Hz,3H),1.20–2.42(m,26H), 2.17(d,J=2.8 Hz,1H),2.20(dd,J=18.3,11.2 Hz,1H),2.29(t,J=7.5 Hz,2H), 2.53(dt,J=1.4,7.9 Hz,2H),2.81(dd,J=18.3,7.6 Hz,1H),2.96 (dt,J=7.6,11.2 Hz,1H),3.48–3.57(m,1H),3.66(s,3H),5.42(dd, J=14.8,9.0 Hz,1H),5.62(ddd,J=14.8,9.0,5.4 Hz,1H)

IR(neat) cm$^{-1}$; 3535,2930,2859,1740,1456,1436,1376, 1243,1173,1067,1029, 970,876,724

Compound 51:

$^1$H-NMR(CDCl$_3$,300 MHz) δ ppm; 0.94(t,J=6.9 Hz,3H), 0.98(t,J=7.4 Hz,3H),1.20–2.13(m,27H), 2.11(d,J=3.3 Hz,1H),2.29(t,J=7.5 Hz,2H),2.48(t,J=7.2 Hz,2H), 2.59(dd, J=18.6,6.6 Hz,1H),2.77–2,.88(m,1H),3.47–3.56(m,1H),3.66 (s,3H),5.54–5.70(m,2H)

IR(neat) cm$^{-1}$; 3523,2930,2859,1740,1456,1436,1376, 1198,1170,1070,972, 726

EXAMPLE 11

(11R,16S)-11,15-Dideoxy-11-propylthio-16-hydroxy-17,17-trimethylene-PGE$_1$ (Compound 52)

Following the substantially same manner as in Example 2 using (11R,16S)-11,15-dideoxy-11-propylthio-16-hydroxy-17,17-trimethylene-PGE$_1$ methyl ester obtained in Example 10, thereby the title compound was obtained.

$^1$H-NMR(CDCl$_3$,300 MHz) δ ppm; 0.94(t,J=6.7 Hz,3H), 0.98(t,J=7.3 Hz,3H),1.20–2.13(m,26H), 2.20(dd,J=18.3, 11.2 Hz,1H),2.23–2.42(m,2H), 2.34(t,J=7.5 Hz,2H),2.53(dt, J=1.4,7.3 Hz,2H), 2.81(dd,J=18.3,7.5 Hz,1H),2.89–3.03(m, 1H), 3.55(dd,J=9.9,2.2 Hz,1H),5.43(dd,J=15.3,8.8 Hz,1H), 5.63(ddd,J=15.3,8.5,5.1 Hz,1H)

IR(neat) cm$^{-1}$; 3467,2930,2859,1740,1708,1456,1402, 1282,1239,1180,1067, 1030,969,875,724

EXAMPLE 12

(11RS,16S)-11,15-Dideoxy-11-acetylthio-16-hydroxy-17,17-trimethylene-PGE$_1$ methyl ester (Compound 53)

Following the substantially same manner as in Example 1(5) using the compound obtained in Example 3(1) and thioacetic acid in place of 2-mercaptoethanol in Example 1(5), thereby the title compound was obtained.

$^1$H-NMR(CDCl$_3$,300 MHz) δ ppm; 0.94(t,J=6.9 Hz,3H), 1.20–2.50(m,26H), 2.13(dd,J=18.9,11.4 Hz,1H),2.29(t,J=7.5 Hz,2H),2.34(s,3H), 2.84–3.00(m,1H),3.46–3.56(m,1H), 3.59–3.74(m,1H), 3.66(s,3H), 5.40(dd,J=15.3,8.9 Hz,1H), 5.63(ddd,J=15.3,8.6,5.8 Hz,1H)

IR(neat) cm$^{-1}$; 3544,2930,2858,1741,1692,1435,1384, 1355,1171,1126,969, 631

EXAMPLE 13

(11R,16S)-11,15-Dideoxy-11-[(2R)-2-methoxycarbonyl-2-aminoethylthio]-16-hydroxy-17, 17-trimethylene-PGE$_1$ methyl ester (Compound 54) and (11S,16S)-11,15-dideoxy-11-[(2R)-2-methoxycarbonyl-2-aminoethylthio]-16-hydroxy-17, 17-trimethylene-PGE$_1$ methyl ester (Compound 55)

Following the substantially same manner as in Example 1(5) using the compound obtained in Example 3(1) and L-cysteine methyl ester in place of 2-mercaptoethanol in Example 1(5), thereby the title compounds were obtained.

Compound 54:

$^1$H-NMR(CDCl$_3$,300 MHz) δ ppm; 0.94(t,J=6.9 Hz,3H), 1.18–2.06(m,25H), 2.14(dd,J=18.5,11.5 Hz,1H),2.22–2.43 (m,2H), 2.29(t,J=7.5 Hz,2H),2.75–2.87(m,1H),2.91–3.08 (m,3H), 3.53(dd,J=10.4,2.0 Hz,1H),3.66(s,3H),3.67(dd,J= 6.5,4.9 Hz, 1H),3.75(s,3H),5.34–5.45(m,1H),5.59–5.72(m, 1H)

IR(neat) cm$^{-1}$; 3368,2930,2858,1740,1594,1436,1198, 1174,1071,1011,970, 876

Compound 55:

$^1$H-NMR(CDCl$_3$,300 MHz) δ ppm; 0.94(t,J=6.8 Hz,3H), 1.20–2.07(m,25H),2.24–2.34(m,2H), 2.29(t,J=7.5 Hz,2H), 2.44–2.55(m,1H), 2.61(dd,J=18.8,7.2 Hz,1H),2.77–2.88(m, 1H), 2.84(dd,J=13.2,7.1 Hz,1H),2.96(dd,J=13.2,5.2 Hz,1H), 3.48–3.70(m,2H),3.66(s,3H),3.76(s,3H),5.57–5.71(m,2H)

IR(neat) cm$^{-1}$; 3377,2930,2858,1739,1436,1198,1174, 1071,1101,973

EXAMPLE 14

(11R,16S)-11,15-Dideoxy-11-(3-nitrophenylthio)-16-hydroxy-17,17-trimethylene-PGE$_1$ methyl ester (Compound 56)

Following the substantially same manner as in Example 1(5) using the compound obtained in Example 3(1) and 3-nitrobenzenethiol in place of 2-mercaptoethanol in Example 1(5), thereby the title compound was obtained.

$^1$H-NMR(CDCl$_3$,300 MHz) δ ppm; 0.94(t,J=6.8 Hz,3H), 1.18–2.16(m,23H),2.19–2.36(m,1H), 2.26(dd,J=18.7,10.7 Hz,1H),2.30(t,J=7.4 Hz,2H),2.44–2.58(m,1H),2.98(dd,J= 18.7,7.6 Hz,1H),3.50–3.69(m,2H),3.67(s,3H),5.48(dd,J= 15.0,9.6 Hz,1H),5.66–5.80(m,1H),7.32–7.66(m,2H), 8.08–8.24(m,2H)

IR(neat) cm$^{-1}$; 3523,2930,1740,1577,1514,1436,1338, 1091,852,742

EXAMPLE 15

(11R,16S)-11,15-Dideoxy-11-(4-methoxybenzylthio)-16-hydroxy-17,17-trimethylene-PGE$_1$ methyl ester (Compound 57) and (11S,16S)-11,15-dideoxy-11-(4-methoxybenzylthio)-16-hydroxy-17,17-trimethylene-PGE$_1$ methyl ester (Compound 58)

Following the substantially same manner as in Example 1(5) using the compound obtained in Example 3(1) and 4-methoxy-α-toluenethiol in place of 2-mercaptoethanol in Example 1(5), thereby the title compounds were obtained.

Compound 57:

$^1$H-NMR(CDCl$_3$,300 MHz) δ ppm; 0.95(t,J=6.9 Hz,3H), 1.16–2.17(m,23H), 2.10(dd,J=18.7,11.3 Hz,1H),2.12(d,J= 2.8 Hz,1H),2.22–2.41(m,2H),2.28(t,J=7.5 Hz,1H), 2.54–2.66(m,1H), 2.81(dt,J=7.5,11.3 Hz,1H),3.48–3.57(m, 1H),3.66(s,3H), 3.74(s,2H),3.80(s,3H),5.33(dd,J=15.2,9.4 Hz,1H),5.58(ddd, J=15.2,9.2,5.4 Hz,1H),6.80–6.87(m,2H), 7.18–7.25(m,2H)

IR(neat) cm$^{-1}$; 3535,2930,2858,1739,1610,1584,1510, 1465,1438,1362,1301, 1250,1174,1098,1067,1034,970,877, 831,745,675,546,517

Compound 58:

$^1$H-NMR(CDCl$_3$,300 MHz) δ ppm; 0.95(t,J=6.9 Hz,3H), 1.18–2.16(m,21H),2.12(d,J=3.3 Hz,1H), 2.20–2.34(m,2H), 2.29(t,J=7.5 Hz,2H),2.38–2.55(m,2H), 2.72–2.83(m,1H), 3.28–3.38(m,1H),3.45–3.54(m,1H), 3.64(d,J=13.4 Hz,1H), 3.73(d,J=13.4 Hz,1H),3.66(s,3H),3.80(s,3H),5.49–5.67(m, 2H),6.80–6.88(m,2H),7.17–7.24(m,2H)

IR(neat) cm$^{-1}$; 3523,2930,2858,1739,1610,1584,1510, 1465,1438,1362,1301, 1250,1174,1107,1070,1034,973,832, 735

EXAMPLE 16

(11R,16S)-11,15-Dideoxy-11-(4-methoxybenzylthio)-16-hydroxy-17,17-trimethylene-PGE$_1$ (Compound 59)

Following the substantially same manner as in Example 2 using (11R,16S)-11,15-dideoxy-11-(4-methoxybenzylthio)-16-hydroxy-17,17-trimethylene-PGE$_1$ methyl ester (Compound 57) obtained in Example 15, thereby the title compound was obtained.

$^1$H-NMR(CDCl$_3$,300 MHz) δ ppm; 0.95(t,J=6.8 Hz,3H), 1.21–2.13(m,25H), 2.11(dd,J=18.6,11.1 Hz,1H),2.22–2.41 (m,1H), 2.33(t,J=7.5 Hz,2H),2.54–2.66(m,1H),2.75–2.87 (m,1H), 3.54(dd,J=10.3,2.3 Hz,1H),3.74(s,2H),3.80(s,3H), 5.28–5.40(m,1H),5.51–5.64(m,1H),6.80–6.88(m,2H), 7.17–7.27(m,2H)

IR(neat) cm$^{-1}$; 3467,2930,2858,1739,1708,1610,1584, 1510,1465,1440,1301, 1249,1175,1067,1034,970,875,831, 745,675,516

EXAMPLE 17

(11R,16R)-3-Oxa-11,15-dideoxy-11-(2-hydroxyethylthio)-16-hydroxy-17,17-trimethylene-PGE$_1$ methyl ester (Compound 64) and (11S,16R)-3-oxa-11,15-dideoxy-11-(2-hydroxyethylthio)-16-hydroxy-17,17-trimethylene-PGE$_1$ methyl ester (Compound 65)

(1) Following the substantially same manner as in Example 1(2) using 5-methoxycarbonyl-4-oxapentyl zinc (II) iodide in place of 5-methoxycarbonylpentyl zinc (II) iodide in Example 1(2), thereby (16RS)-3-oxa-15-deoxy-16-hydroxy-17,17-trimethylene-PGE$_1$ methyl ester 11,16-bis(tert-butyldimethylsilyl ether) was obtained.

$^1$H-NMR(CDCl$_3$,200 MHz) δ ppm; 0.01–0.08(m,12H), 0.78–0.98(m,3H),0.88(s,9H),0.91(s,9/2H), 0.92(s,9/2H), 1.15–2.25(m,19H),2.16(dd,J=18.1,8.0 Hz,1H), 2.32–2.50 (m,1H),2.60(ddd,J=18.1,7.0,1.0 Hz,1H),3.43–3.65(m,1H), 3.50(t,J=6.5 Hz,2H),3.75(s,3H),3.91–4.08(m,1H),4.06(s,2H),5.21–5.38(m,1H),5.51–5.73(m,1H)

IR(neat) cm$^{-1}$; 2955,2930,2857,1745,1472,1463,1436, 1406,1361,1256,1207, 1142,1099,1006,972,938,881,836, 811,775,705,669,577

(2) Following the substantially same manner as in Example 1(3) using the compound obtained in (1), thereby the compounds described below were obtained.

(16R)-3-Oxa-15-deoxy-16-hydroxy-17,17-trimethylene-PGE$_1$ methyl ester $^1$H-NMR(CDCl$_3$,300 MHz) δ ppm; 0.94(t,J=6.9 Hz,3H), 1.23–2.43(m,22H), 2.24(dd,J=18.5,9.6 Hz,1H), 2.75(ddd,J=18.5,7.4,1.3 Hz,1H),3.47–3.64(m,1H),3.52(t,J=6.1 Hz,2H), 3.75(s,3H),3.99–4.17(m,1H),4.07(s,2H),5.49(dd,J=15.1,8.5 Hz,1H), 5.75(ddd,J=15.1,8.3,6.1 Hz,1H)

IR(neat) cm$^{-1}$; 3435,2953,2869,1741,1438,1282,1214, 1139,1075,1032,973, 882,706,579

(16S)-3-Oxa-15-deoxy-16-hydroxy-17,17-trimethylene-PGE$_1$ methyl ester $^1$H-NMR(CDCl$_3$,300 MHz) δ ppm; 0.95(t,J=6.9 Hz,3H), 1.28–2.44(m,21H), 2.22(dd,J=18.5,9.6 Hz,1H),2.67–2.85 (br,1H), 2.73(dd,J=18.5,8.0 Hz,1H),3.51(t,J=6.3 Hz,2H), 3.57(dd,J=10.3,2.3 Hz,1H),3.75(s,3H),3.97–4.10(m,1H), 4.07(s,2H),5.44(dd,J=15.1,8.4 Hz,1H),5.73(ddd, J=15.1,8.4, 6.2 Hz,1H)

IR(neat) cm$^{-1}$; 3400,2952,2869,1740,1437,1348,1282, 1213,1140,1074,1032, 969,881,706,579

(3) Following the substantially same manner as in Example 1(4) using (16R)-3-oxa-15-deoxy-16-hydroxy-17, 17-trimethylene-PGE$_1$ methyl ester obtained in (2), thereby (16R)-3-oxa-15-deoxy-16-hydroxy-17,17-trimethylene-PGE$_1$ methyl ester was obtained.

$^1$H-NMR(CDCl$_3$,300 MHz) δ ppm; 0.90–0.98(m,3H), 1.23–2.29(m,18H),3.23–3.30(m,1H),3.48–3.59(m,1H),3.53 (t,J=6.3 Hz,2H),3.75(s,3H),4.08(s,2H),5.43–5.55(m,1H), 5.58–5.74(m,1H),6.15(dd,J=5.6,2.0 Hz,1H), 7.48(dd,J=5.6 Hz,2.4 Hz,1H)

IR(neat) cm$^{-1}$; 3501,2933,2869,1755,1703,1587,1456, 1437,1397,1351,1281, 1211,1140,1068,1031,972,886,802, 741,706,580

(4) Following the substantially same manner as in Example 1(5) using the compound obtained in (3), thereby the title compounds were obtained.

Compound 64:

$^1$H-NMR(CDCl$_3$,300 MHz) δ ppm; 0.94(t,J=7.0 Hz,3H), 1.22–2.46(m,22H), 2.20(dd,J=18.7,11.2 Hz,1H),2.73–2.89 (m,3H),2.96–3.09(m,1H),3.47–3.62(m,1H),3.51(t,J=6.2 Hz,2H), 3.68–3.79(m,2H),3.75(s,3H),4.07(s,2H),5.42–5.53 (m,1H),5.67–5.80(m,1H)

IR(neat) cm$^{-1}$; 3459,2952,2869,1740,1437,1401,1283, 1214,1138,1047,972, 885,706

Compound 65:

$^1$H-NMR(CDCl$_3$,300 MHz) δ ppm; 0.94(t,J=6.9 Hz,3H), 1.23–2.92(m,26H),3.47–3.62(m,2H), 3.51(t,J=6.2 Hz,2H), 3.69–3.80(m,2H),3.75(s,3H),4.07(s,2H), 5.55–5.77(m,2H)

IR(neat) cm$^{-1}$; 3459,2930,2869,1740,1436,1400,1283, 1214,1138,1048,975, 885,706,580

EXAMPLE 18

(11R,16R)-3-Oxa-11,15-dideoxy-11-(2-hydroxyethylthio)-16-hydroxy-17,17-trimethylene-PGE$_1$ (Compound 66)

Following the substantially same manner as in Example 2 using (11R,16R)-3-oxa-11,15-dideoxy-11-(2-hydroxyethylthio)-16-hydroxy-17,17-trimethylene-PGE$_1$ methyl ester obtained in Example 17, thereby the title compound was obtained.

$^1$H-NMR(CDCl$_3$,300 MHz) δ ppm; 0.94(t,J=6.8 Hz,3H), 1.22–2.47(m,20H), 2.21(dd,J=18.5,11.2 Hz,1H),2.72–3.78 (m,7H), 3.55(t,J=5.5 Hz,2H),3.66(dd,J=10.0,2.4 Hz,1H), 3.74(t,J=6.0 Hz,2H),4.06(s,2H),5.41–5.52(m,1H),5.62–5.79 (m,1H)

IR(neat) cm$^{-1}$; 3437,2930,2870,1739,1455,1430,1402, 1279,1223,1134,1048, 970,876,755,675

EXAMPLE 19

(11R,16S)-3-Oxa-11,15-dideoxy-11-(2-hydroxyethylthio)-16-hydroxy-17,17-trimethylene-PGE$_1$ methyl ester (Compound 67) and (11S,16S)-3-oxa-11,15-dideoxy-11-(2-hydroxyethylthio)-16-hydroxy-17,17-trimethylene-PGE$_1$ methyl ester (Compound 68)

(1) Following the substantially same manner as in Example 1(4) using (16S)-3-oxa-15-deoxy-16-hydroxy-17, 17-trimethylene-PGE$_1$ methyl ester obtained in Example 17(2), thereby (16S)-3-oxa-15-deoxy-16-hydroxy-17,17-trimethylene-PGE$_1$ methyl ester was obtained.

$^1$H-NMR(CDCl$_3$,300 MHz) δ ppm; 0.94(t,J=6.9 Hz,3H), 1.23–2.28(m,20H),3.22–3.30(m,1H), 3.48–3.58(m,1H),3.53 (t,J=6.3 Hz,2H), 3.75(s,3H), 4.08(s,2H),5.48(dd,J=15.4,8.1 Hz,1H),5.63–5.76(m,1H), 6.15(dd,J=5.7,2.1 Hz,1H),7.48 (dd,J=5.7 Hz,2.4 Hz,1H)

IR(neat) cm$^{-1}$; 3498,2933,2869,1755,1706,1587,1437, 1384,1350,1281,1210, 1140,1068,1031,973,886,809,705, 579

(2) Following the substantially same manner as in Example 1(5) using the compound obtained in (1), thereby the title compounds were obtained.

Compound 67:

$^1$H-NMR(CDCl$_3$,200 MHz) δ ppm; 0.94(t,J=6.8 Hz,3H), 1.21–2.48(m,21H), 2.20(dd,J=18.5,11.2 Hz,1H),2.52–3.11 (m,5H),3.45–3.64(m,1H),3.51(t,J=6.3 Hz,2H),3.67–3.86(m, 2H), 3.75(s,3H),4.07(s,2H),5.42(dd,J=15.2,9.1 Hz,1H), 5.68 (ddd,J=15.2,9.2,5.2 Hz,1H)

IR(neat) cm$^{-1}$; 3467,2952,2869,1740,1437,1401,1384, 1282,1213,1138,1048, 971,876,741

Compound 68:

$^1$H-NMR(CDCl$_3$,200 MHz) δ ppm; 0.87–1.00(m,3H), 1.21–2.95(m,26H),3.43–3.66(m,1H), 3.54(t,J=6.3 Hz,2H), 3.67–3.83(m,2H),3.76(s,3H),3.85–3.98(m,1H),4.07(s,2H), 5.55–5.77(m,2H)

IR(neat) cm$^{-1}$; 3453,2930,2869,1740,1437,1399,1282, 1214,1139,1048,974, 885,706,580

EXAMPLE 20

(11R,16S)-3-Oxa-11,15-dideoxy-11-(2-hydroxyethylthio)-16-hydroxy-17,17-trimethylene-PGE$_1$ (Compound 69)

Following the substantially same manner as in Example 2 using (11R,16S)-3-oxa-11,15-dideoxy-11-(2- hydroxyethylthio)-16-hydroxy-17,17-trimethylene-PGE₁ methyl ester obtained in Example 19, thereby the title compound was obtained.

¹H-NMR(CDCl₃,300 MHz) δ ppm; 0.94(t,J=6.9 Hz,3H), 1.22–3.43(m,27H), 2.21(dd,J=18.7,11.3 Hz,1H),3.52–3.63 (m,1H), 3.56(t,J=5.8 Hz,2H),3.74(t,J=5.9 Hz,2H),4.01–4.15 (m,2H), 5.38–5.51(m,1H),5.63–5.75(m,1H)

IR(neat) cm⁻¹; 3443,2930,2870,1739,1455,1430,1402, 1278,1223,1135,1049, 970,876,756,667,577

EXAMPLE 21

(11R,16S)-3-Oxa-11,15-dideoxy-11-(2-hydroxyethylthio)-16-hydroxy-17,17-tetramethylene-PGE₁ methyl ester (Compound 70) and (11S,16S)-3-oxa-11,15-dideoxy-11-(2-hydroxyethylthio)-16-hydroxy-17,17-tetramethylene-PGE₁ methyl ester (Compound 71)

(1) Following the substantially same manner as in Example 1(1) using (1E,4RS)-1-iodo-4-(tert-butyldimethylsiloxy)-5,5-tetramethylene-1-octene in place of (1E,4RS)-1-iodo-4-(tert-butyldimethylsiloxy)-5,5-trimethylene-1-octene in Example 1(1), thereby (3R,4R)-2-ethylene-3-[(1E,4RS)-4-tert-butyldimethylsiloxy-5,5-tetramethyleneoct-1-eny]-4-(tert-utyldimethylsiloxy) cyclopentan-1-one was obtained.

¹H-NMR(CDCl₃,200 MHz) δ ppm; 0.04(s,9H),0.05(s, 9H),0.79–1.72(m,15H), 0.88(s,9H), 0.89(s,9H),2.15–2.47 (m,3H),2.56–2.72(m,1H),3.19–3.33(m,1H),3.50–3.64(m, 1H), 3.98–4.14(m,1H),5.21–5.37(m,2H),5.63–5.85(m,1H), 6.06–6.14(m,1H)

IR(neat) cm⁻¹; 2955,2930,2858,1734,1641,1472,1463, 1387,1361,1255,1190, 1087,1006,972,939,880,836,812, 774,669

(2) Following the substantially same manner as in Example 1(2) using the compound obtained in (1) and 5-methoxycarbonyl-4-oxapentyl zinc (II) iodide in place of 5-methoxycarbonylpentyl zinc (II) iodide in Example 1(2), thereby (16RS)-3-oxa-15-deoxy-16-hydroxy-17,17-tetramethylene-PGE₁ methyl ester 11,16-bis(tert-butyldimethylsilyl ether) was obtained.

¹H-NMR(CDCl₃,200 MHz) δ ppm; 0.03(s,3H),0.04(s, 6H),0.06(s,3H),0.78–1.72(m,21H), 0.88(s,9H),0.89(s,9H), 1.86–2.04(m,1H),2.06–2.51(m,3H), 2.17(dd,J=18.2,8.1 Hz,1H),2.61(ddd,J=18.2,6.9,1.2 Hz,1H), 3.42–3.65(m,3H), 3.75(s,3H),3.92–4.13(m,1H),4.07(s,2H), 5.22–5.39(m,1H), 5.61–5.80(m,1H)

IR(neat) cm⁻¹; 2954,2930,2858,1745,1472,1462,1438, 1361,1255,1207,1142, 1099,1006,973,938,881,837,812, 775,669

(3) Following the substantially same manner as in example 1(3) using the compound obtained in (2), thereby the compounds described below were obtained.

(16R)-3-Oxa-15-deoxy-16-hydroxy-17,17-tetramethylene-PGE₁ methyl ester

¹H-NMR(CDCl₃+D₂O,300 MHz) δ ppm; 0.90(t,J=6.8 Hz,3H),1.20–1.76(m,18H),1.96–2.14(m,2H), 2.23(dd,J= 18.3,9.6 Hz,1H),2.30–2.45(m,2H), 2.74(dd,J=18.3,7.5 Hz,1H),3.46–3.57(m,1H), 3.51(t,J=6.2 Hz,2H),3.75(s,3H), 3.98–4.17(m,1H), 4.07(s,2H),5.48(dd,J=15.4,8.7 Hz,1H), 5.71(ddd,J=15.4,7.9, 5.5 Hz,1H)

IR(neat) cm⁻¹; 3436,2952,2869,1740,1455,1439,1283, 1213,1138,1075,974, 883,706,579,429

(16S)-3-Oxa-15-deoxy-16-hydroxy-17,17-tetramethylene-PGE₁ methyl ester

¹H-NMR(CDCl₃+D₂O,300 MHz) δ ppm; 0.91(t,J=6.8 Hz,3H),1.20–1.73(m,18H),1.93–2.13(m,2H),2.22(dd,J= 18.4,9.9 Hz,1H),2.30–2.43(m,2H),2.72(ddd,J=18.4,7.5,1.2 Hz,1H),3.46–3.54(m,1H), 3.51(t,J=6.4 Hz,2H),3.75(s,3H), 3.97–4.17(m,1H),4.07(s,2H), 5.42(dd,J=15.3,8.5 Hz,1H), 5.71(ddd,J=15.3,8.8,5.7 Hz,1H)

IR(neat) cm⁻¹; 3400,2952,2869,1742,1438,1282,1211, 1140,1073,967,883,705,579

(4) Following the substantially same manner as in Example 1(4) using (16S)-3-oxa-15-deoxy-16-hydroxy-17, 17-tetramethylene-PGE₁ methyl ester obtained in (3), thereby (16S)-3-oxa-15-deoxy-16-hydroxy-17,17-tetramethylene-PGE₁ methyl ester was obtained.

¹H-NMR(CDCl₃+D₂O,300 MHz) δ ppm; 0.89(t,J=6.8 Hz,3H),1.19–1.90(m,18H),1.96–2.13(m,2H), 2.29(dd,J= 14.6,6.4 Hz,1H),3.22–3.30(m,1H), 3.46(dd,J=10.4,2.2 Hz,1H),3.53(t,J=6.4 Hz,2H), 3.75(s,3H),4.07(s,2H),5.47 (dd,J=15.4,8.3 Hz,1H), 5.70(dt,J=15.4,7.1 Hz,1H),6.14(dd, J=5.7,2.0 Hz,1H), 7.48(dd,J=5.7,2.6 Hz,1H)

IR(neat) cm⁻¹; 3519,2951,2869,1756,1704,1587,1455, 1438,1376,1350,1281, 1210,1141,1062,974,885,809,742, 706,579

(5) Following the substantially same manner as in Example 1(5) using the compound obtained in (4), thereby the title compounds were obtained.

Compound 70:

¹H-NMR(CDCl₃+D₂O,300 MHz) δ ppm; 0.90(t,J=6.8 Hz,3H),1.20–1.71(m,18H),1.95–2.11(m,1H), 2.20(dd,J= 18.6,11.3 Hz,1H),2.30–2.44(m,2H),2.69–2.90(m,4H), 2.95–3.09(m,1H),3.41–3.56(m,1H), 3.51(t,J=6.3 Hz,2H), 3.72(t,J=6.0 Hz,2H),3.75(s,3H), 4.07(s,2H),5.41(dd,J=15.2, 9.4 Hz,1H), 5.66(ddd,J=15.2,9.5,5.2 Hz,1H)

IR(neat) cm⁻¹; 3464,2952,2869,1740,1438,1401,1283, 1212,1139,1046,971, 882,706

Compound 71:

¹H-NMR(CDCl₃+D₂O,300 MHz) δ ppm; 0.90(t,J=6.9 Hz,3H),1.19–1.69(m,18H),1.96–2.10(m,1H), 2.24–2.93(m, 7H), 3.46(dd,J=11.0,2.0 Hz,1H), 3.51(t,J=6.4 Hz,2H), 3.55–3.64(m,1H),3.74(t,J=5.8 Hz,2H), 3.75(s,3H),4.07(s, 2H),5.57–5.73(m,2H)

IR(neat) cm⁻¹; 3436,2951,2869,1740,1438,1400,1282, 1214,1139,1046,976, 705,579

EXAMPLE 22

(11R,16S)-3-Oxa-11,15-dideoxy-11-(2-hydroxyethylthio)-16-hydroxy-17,17-tetramethylene-PGE₁ (Compound 72)

Following the substantially same manner as in Example 2 using (11R,16S)-3-oxa-11,15-dideoxy-11-(2-hydroxyethylthio)-16-hydroxy-17,17-tetramethylene-PGE₁ methyl ester obtained in Example 21, thereby the title compound was obtained.

¹H-NMR(CDCl₃+D₂O,300 MHz) δ ppm; 0.90(t,J=6.9 Hz,3H),1.18–1.70(m,21H),1.98–2.13(m,1H), 2.20(dd,J= 18.4,11.3 Hz,1H),2.31–2.46(m,2H),2.70–2.92(m,4H), 2.94–3.08(m,1H),3.47–3.61(m,1H), 3.56(t,J=5.4 Hz,2H), 3.74(t,J=5.8 Hz,2H), 4.07(s,2H),5.43(dd,J=14.8,8.9 Hz,1H), 5.60–5.76(m,1H)

IR(neat) cm⁻¹; 3453,2952,2869,1739,1455,1430,1402, 1223,1135,1046,970, 880,756,676

EXAMPLE 23

(11R,16R)-3-Oxa-11,15-dideoxy-11-(2-hydroxyethylthio)-16-hydroxy-17,17-tetramethylene-PGE₁ methyl ester (Compound 73) and (11S,16R)-3-oxa-11,15-dideoxy-11-(2-hydroxyethylthio)-16-hydroxy-17,17-tetramethylene-PGE₁ methyl ester (Compound 74)

(1) Following the substantially same manner as in Example 1(4) using (16R)-3-oxa-15-deoxy-16-hydroxy-17, 17-tetramethylene-PGE$_1$ methyl ester obtained in Example 21(3), thereby (16R)-3-oxa-15-deoxy-16-hydroxy-17,17-tetramethylene-PGA$_1$ methyl ester was obtained.

1H-NMR(CDCl$_3$+D$_2$O,300 MHz) δ ppm; 0.89(t,J=6.8 Hz,3H),1.18–1.92(m,18H),1.97–2.13(m,2H), 2.30(dd,J= 14.1,5.4 Hz,1H),3.22–3.30(m,1H), 3.46(dd,J=10.4,1.9 Hz,1H),3.53(t,J=6.2 Hz,2H), 3.76(s,3H),4.08(s,2H),5.49 (dd,J=15.3,8.0 Hz,1H), 5.66(ddd,J=15.3,7.8,5.9 Hz,1H), 6.15(dd,J=5.7,1.9 Hz,1H), 7.48(dd,J=5.7,2.4 Hz,1H)

IR(neat) cm$^{-1}$; 3497,2952,2868,1755,1702,1587,1546, 1438,1384,1350,1281, 1210,1139,1062,972,884,806,705

(2) Following the substantially same manner as in Example 1(5) using the compound obtained in (1), thereby the title compounds were obtained.

Compound 73:

$^1$H-NMR(CDCl$_3$+D$_2$O,300 MHz) δ ppm; 0.90(t,J=6.8 Hz,3H),1.18–1.70(m,18H),1.98–2.16(m,2H), 2.20(dd,J= 18.5,11.2 Hz,1H),2.27–2.46(m,2H),2.72–2.89(m,3H), 2.96–3.09(m,1H),3.47–3.56(m,1H), 3.51(t,J=6.2 Hz,2H), 3.72(t,J=6.0 Hz,2H),3.75(s,3H),4.07(s, 2H),5.47(dd,J=15.2, 8.6 Hz,1H), 5.75(ddd,J=15.2,8.1,5.8 Hz,1H)

IR(neat) cm$^{-1}$; 3459,2952,2869,1740,1455,1438,1401, 1283,1213,1138,1046, 974,884,706

Compound 74:

$^1$H-NMR(CDCl$_3$+D$_2$O,300 MHz) δ ppm; 0.90(t,J=6.8 Hz,3H),1.19–1.69(m,18H),2.00–2.14(m,1H), 2.30–2.43(m, 2H), 2.49–2.93(m,4H),2.74(dt,J=4.2,5.9 Hz,1H), 3.44–3.55 (m,1H),3.51(t,J=6.2 Hz,2H),3.56–3.63(m,1H), 3.74(t,J=5.9 Hz,2H),3.75(s,3H),4.07(s,2H),5.62(ddd,J=15.5, 7.8,5.1 Hz,1H),5.72(dd,J=15.5,6.7 Hz,1H)

IR(neat) cm$^{-1}$; 3453,2951,2869,1740,1455,1438,1400, 1282,1214,1138,1046, 977,884,706,580

EXAMPLE 24

(11R,16R)-3-Oxa-11,15-dideoxy-11-(2-hydroxyethylthio)-16-hydroxy-17,17-tetramethylene-PGE$_1$ (Compound 75)

Following the substantially same manner as in Example 2 using (11R,16R)-3-oxa-11,15-dideoxy-11-(2-hydroxyethylthio)-16-hydroxy-17,17-tetramethylene-PGE$_1$ methyl ester obtained in Example 23, thereby the title compound was obtained.

$^1$H-NMR(CDCl$_3$,300 MHz) δ ppm; 0.90(t,J=6.9 Hz,3H), 1.18–1.72(m,21H),1.98–2.18(m,1H), 2.21(dd,J=18.6,11.3 Hz,1H),2.29–2.47(m,2H),2.72–2.93(m,2H),2.80(dt,J=1.9, 6.0 Hz,2H),2.95–3.08(m,1H), 3.54(t,J=5.6 Hz,2H),3.59(dd, J=10.6,1.9 Hz,1H), 3.74(t,J=6.0 Hz,2H),4.06(s,2H),5.46(dd, J=15.3,9.2 Hz,1H), 5.73(ddd,J=15.3,8.5,5.6 Hz,1H)

IR(neat) cm$^{-1}$; 3435,2951,2869,1739,1455,1402,1281, 1223,1133,1046,969, 881,676

EXAMPLE 25

(11R,16RS)-11,15-Dideoxy-11-(2-hydroxyethylthio)-16-hydroxy-17,17-trimethylene-13,14-didehydro-PGE$_1$ methyl ester (Compound 85) and (11S,16RS)-11,15-dideoxy-11-(2-hydroxyethylthio)-16-hydroxy-17,17-trimethylene-13,14-didehydro-PGE$_1$ methyl ester (Compound 86)

(1) A toluene solution (12 ml) of (4RS)-4-(tert-butyldimethylsiloxy)-5,5-trimethylene-1-octyne (1.09 g) was added n-butyl lithium (2.5 M, hexane solution, 1.44 ml) under an argon stream at 0° C., followed by stirring at room temperature for 30 minutes. To the solution was added diethylaluminum chloride (0.95 M, hexane solution, 4.42 ml) at 0° C., followed by stirring at room temperature for 30 minutes. To the solution was added dropwise (4R)-2-(N,N-diethylamino)methyl-4-(tert-butyldimethylsiloxy) cyclopent-2-en-1-one (0.25 M, toluene solution, 12.0 ml) at 0° C., followed by stirring at room temperature for 20 minutes. The reaction solution was poured into a mixture of hexane (32 ml), a saturated aqueous ammonium chloride solution (32 ml) and hydrochloric acid (3M) (9 ml) with stirring, the organic layer was separated, and the aqueous layer was extracted with hexane (150 ml). The resulting organic layers were combined, washed with a saturated aqueous sodium bicarbonate solution and a saturated aqueous sodium chloride solution, dried over anhydrous magnesium sulfate and filtered. The filtrate was concentrated under reduced pressure, and the resulting crude product was purified by a silica gel column chromatography (developing solvent; hexane:ethyl acetate=49:1) to give (3R,4R)-2-methylene-3-[(4RS)-4-tert-butyldimethylsiloxy-5,5-trimethyleneoct-1-ynyl]-4-(tert-butyldimethylsiloxy) cyclopentan-1-one (620 mg).

$^1$H-NMR(CDCl$_3$,300 MHz) δ ppm; 0.08(s,3H),0.10(s, 3H),0.11(s,3H),0.13(s,3H),0.80–0.98(m,3H),0.89(s,9H), 0.90(s,9H),1.20–2.39(m,12H), 2.31(dd,J=18.0,7.1 Hz,1H), 2.70(dd,J=18.0,6.2 Hz,1H), 3.42–3.50(m,1H),3.71(t,J=5.0 Hz,1H),4.21–4.30(m,1H),5.53(d,J=2.7 Hz,1H),6.12(d,J=2.9 Hz,1H)

IR(CHCl$_3$) cm$^{-1}$; 2956,2931,2895,2858,2218,1735,1713, 1622,1472,1464,1362, 1256,1094,1006,931,837,776,671

(2) Following the substantially same manner as in Example 1(2) using the compound obtained in (1) in place of (3R,4R)-2-methylene-3-[(1E,4RS)-4-tert-butyldimethylsiloxy-5,5-trimethyleneoct-1-enyl]-4-(tert-butyldimethylsiloxy)cyclopentan-1-one in Example 1(2), thereby (16RS)-15-deoxy-16-hydroxy-17,17-trimethylene-13,14-didehydro-PGE$_1$ methyl ester 11,16-bis(tert-butyldimethylsilyl ether) was obtained.

$^1$H-NMR(CDCl$_3$,200 MHz) δ ppm; 0.08(s,3H),0.09(s, 3H),0.12(s,3H),0.13(s,3H),0.81–1.01(m,3H),0.90(s,9H), 0.91(s,9H),1.18–2.41(m,23H)2.15(dd,J=18.1,6.7 Hz,1H), 2.30(t,J=7.5 Hz,2H),2.56–2.76(m,2H),3.65–3.77(m,1H), 3.67(s,3H),4.19–4.36(m,1H)

IR(neat) cm$^{-1}$; 2954,2931,2858,1747,1471,1464,1436, 1362,1255,1165,1098, 1007,938,838,777,670

(3) Following the substantially same manner as in Example 1(3) using the compound obtained in (2), thereby (16RS)-15-deoxy-16-hydroxy-17,17-trimethylene-13,14-didehydro-PGE$_1$ methyl ester was obtained.

$^1$H-NMR(CDCl$_3$,300 MHz) δ ppm; 0.94(t,J=7.0 Hz,3H), 1.23–2.45(m,25H), 2.22(dd,J=18.4,9.2 Hz,1H),2.31(t,J=7.5 Hz,2H),2.56–2.67(m,1H),2.75(ddd,J=18.4,7.3,1.2 Hz,1H), 3.67(s,3H),3.69(dd,J=9.0,3.4 Hz,1H),4.25–4.36(m,1H)

IR(neat) cm$^{-1}$; 3435,2932,2860,2237,1741,1437,1362, 1321,1201,1168,1104, 1076,931,848,726

(4) Following the substantially same manner as in Example 1(4) using the compound obtained in (3), thereby (16RS)-15-deoxy-16-hydroxy-17,17-trimethylene-13,14-didehydro-PGE$_1$ methyl ester was obtained.

$^1$H-NMR(CDCl$_3$,300 MHz) δ ppm; 0.93(t,J=7.0 Hz,3H), 1.22–2.43(m,23H), 2.23(ddd,J=16.6,9.0,2.3 Hz,1H),2.31(t, J=7.4 Hz,2H), 3.36–3.43(m,1H),3.59–3.70(m,1H),3.67(s, 3H), 6.16(dd,J=5.6,2.3 Hz,1H),7.47(dd,J=5.6,2.4 Hz,1H)

IR(neat) cm$^{-1}$; 3468,2932,2859,2242,1736,1712,1590, 1437,1346,1198,1174, 1073,885

(5) Following the substantially same manner as in Example 1(5) using the compound obtained in (4), thereby the title compounds were obtained.

Compound 85:

$^1$H-NMR(CDCl$_3$,300 MHz) δ ppm; 0.94(t,J=7.0 Hz,3H), 1.21–2.44(m,24H),2.30(t,J=7.5 Hz,2H), 2.55–2.97(m,4H), 2.86(dt,J=13.9,6.1 Hz,1H), 3.10(dt,J=13.9,6.2 Hz,1/2H), 3.11(dt,J=13.9,6.3 Hz,1/2H), 3.18–3.36(m,1H),3.56–3.75 (m,1H),3.67(s,3H),3.78–3.89(m,2H)

IR(neat) cm$^{-1}$; 3435,2930,2859,2242,1740,1437,1352, 1202,1170,1045,725

Compound 86:

$^1$H-NMR(CDCl$_3$,300 MHz) δ ppm; 0.93(t,J=7.0 Hz,3H), 1.20–2.64(m,26H),2.30(t,J=7.4 Hz,2H), 2.80(dt,J=13.8,5.6 Hz,1/2H),2.81(dt,J=13.8,5.6 Hz,1/2H), 2.86–2.98(m,2H), 3.02–3.12(m,1H),3.60–3.74(m,1H), 3.67(s,3H), 3.70(dt,J=9.7,3.2 Hz,1H),3.76–3.86(m,2H)

IR(neat) cm$^{-1}$; 3464,2931,2860,2242,1740,1436,1277, 1202,1169,1070,847, 726

EXAMPLE 26

(11R,16RS)-11,15-Dideoxy-11-(2-hydroxyethylthio)-16-hydroxy-17,17-trimethylene-13,14-didehydro-PGE$_1$ (Compound 87)

Following the substantially same manner as in Example 2 using (11R,16RS)-11,15-dideoxy-11-(2-hydroxyethylthio)-16-hydroxy-17,17-trimethylene-13,14-didehydro-PGE$_1$ methyl ester obtained in Example 25, thereby the title compound was obtained.

$^1$H-NMR(CDCl$_3$,300 MHz) δ ppm; 0.94(t,J=7.0 Hz,3H), 1.21–2.44(m,26H), 2.11(ddd,J=18.9,11.7,2.3 Hz,1H),2.35(t, J=7.3 Hz,2H), 2.56–2.69(m,1H),2.73–2.92(m,2H), 3.04–3.16(m,1H), 3.21–3.36(m,1H),3.72(ddd,J=9.7,6.9,3.0 Hz,1H),3.80–3.88(m,2H)

IR(neat) cm$^{-1}$; 3414,2931,2860,2242,1741,1465,1402, 1348,1280,1216,1045, 932,757,666

EXAMPLE 27

(11S,16RS)-11,15-Dideoxy-11-(2-hydroxyethylthio)-16-hydroxy-17,17-trimethylene-13,14-didehydro-PGE$_1$ (Compound 88)

Following the substantially same manner as in Example 2 using (11S,16RS)-11,15-dideoxy-11-(2-hydroxyethylthio)-16-hydroxy-17,17-trimethylene-13,14-didehydro-PGE$_1$ methyl ester obtained in Example 25, thereby the title compound was obtained.

$^1$H-NMR(CDCl$_3$,300 MHz) δ ppm; 0.93(t,J=7.0 Hz,3H), 1.22–2.65(m,28H),2.35(t,J=7.3 Hz,2H), 2.77–2.99(m,2H), 3.03–3.14(m,1H),3.60–3.71(m,1H), 3.71(dd,J=9.6,3.2 Hz,1H),3.78–3.85(m,2H)

IR(neat) cm$^{-1}$; 3436,2932,2860,2237,1739,1465,1402, 1281,1227,1165,1069, 932,726

EXAMPLE 28

(11R,16RS)-3-Oxa-11,15-dideoxy-11-(2-hydroxyethylthio)-16-hydroxy-17,17-tetramethylene-13,14-didehydro-PGE$_1$ methyl ester (Compound 98)

(1) Following the substantially same manner as in Example 25(1) using (4RS)-4-(tert-butyldimethylsiloxy)-5,5-tetramethylene-1-octyne in place of (4RS)-4-(tert-butyldimethylsiloxy)-5,5-trimethylene-1-octyne in Example 25(1), thereby (3R,4R)-2-methylene-3-[(4RS)-4-tert-butyldimethylsiloxy-5,5-tetramethyleneoct-1-ynyl]-4-(tert-butyldimethylsiloxy)cyclopentan-1-one was obtained.

$^1$H-NMR(CDCl$_3$,200 MHz) δ ppm; 0.04–0.16(m,12H), 0.81–0.99(m,3H),0.89(s,9H),0.90(s,9H), 1.16–1.75(m, 12H),2.20–2.40(m,1H), 2.32(dd,J=18.0,7.1 Hz,1H),2.51 (ddd,J=17.2,4.7,2.6 Hz,1H), 2.71(dd,J=18.0,6.4 Hz,1H), 3.43–3.58(m,1H), 3.67(t,J=4.8 Hz,2H),4.20–4.35(m,1H), 5.54(d,J=2.6 Hz,1H), 6.13(d,J=3.1 Hz,1H)

IR(neat) cm$^{-1}$; 2955,2930,2858,2235,1736,1646,1472, 1463,1387,1361,1283, 1252,1221,1186,1121,1089,1006, 940,919,837,776,670,525

(2) Following the substantially same manner as in Example 1(2) using the compound obtained in (1) in place of (3R,4R)-2-methylene-3-[(1E,4RS)-4-tert-butyldimethylsiloxy-5,5-trimethyleneoct-1-enyl]-4-(tert-butyldimethylsiloxy)cyclopentan-1-one in Example 1(2) and using 5-methoxycarbonyl-4-oxapentyl zinc (II) iodide in place of 5-methoxycarbonylpentyl zinc (II) iodide in Example 1(2), thereby (16RS)-3-oxa-15-deoxy-16-hydroxy-17,17-tetramethylene-13,14-didehydro-PGE$_1$ methyl ester 11,16-bis(tert-butyldimethylsilyl ether) was obtained.

$^1$H-NMR(CDCl$_3$,200 MHz) δ ppm; 0.07(s,3H),0.09(s, 3H),0.12(s,6H),0.86–0.96(m,3H),0.89(s,18H),1.15–1.79(m, 18H),2.06–2.78(m,5H),2.16(dd,J=18.0,6.4 Hz,1H),3.52(t,J= 6.5 Hz,2H), 3.65(t,J=4.9 Hz,1H),3.76(s,3H),4.07(s,2H), 4.21–4.35(m,1H)

IR(neat) cm$^{-1}$; 2954,2930,2858,1746,1472,1463,1438, 1406,1375,1361,1252, 1206,1141,1094,1006,920,885,837, 811,776,670,577

(3) Following the substantially same manner as in Example 1(3) using the compound obtained in (2), thereby (16RS)-3-oxa-15-deoxy-16-hydroxy-17,17-tetramethylene-13,14-didehydro-PGE$_1$ methyl ester was obtained.

$^1$H-NMR(CDCl$_3$,300 MHz) δ ppm; 0.90(t,J=6.8 Hz,3H), 1.14–1.89(m,18H),2.16–2.50(m,4H), 2.23(dd,J=18.6,9.0 Hz,1H),2.58–2.74(m,2H), 2.74(ddd,J=18.6,7.0,1.2 Hz,1H), 3.54(t,J=6.1 Hz,2H),3.60–3.69(m,1H),3.76(s,3H),4.08(s, 2H),4.25–4.37(m,1H)

IR(neat) cm$^{-1}$; 3435,2952,2869,1745,1455,1439,1283, 1214,1139,1080,772, 706,580

(4) Following the substantially same manner as in Example 1(4) using the compound obtained in (3), thereby (16RS)-3-oxa-15-deoxy-16-hydroxy-17,17-tetramethylene-13,14-didehydro-PGE$_1$ methyl ester was obtained.

$^1$H-NMR(CDCl$_3$,300 MHz) δ ppm; 0.85–0.95(m,3H), 1.18–2.80(m,23H),3.40–3.60(m,2H),3.73–3.77(m,1H), 3.75 (s,3H),4.02–4.10(m,2H), 5.85(d,J=5.9 Hz,1H),7.78(d,J=5.3 Hz,1H)

IR(neat) cm$^{-1}$; 3468,2952,2869,2217,1755,1698,1610, 1519,1438,1383,1286, 1209,1138,1060,706

(5) Following the substantially same manner as in Example 1(5) using the compound obtained in (4), thereby the title compound was obtained.

Compound 98:

$^1$H-NMR(CDCl$_3$,200 MHz) δ ppm; 0.75–3.02(m,30H), 3.20–3.34(m,1H),3.41–3.88(m,6H),3.75(s,3H),4.08(s,2H)

IR(neat) cm$^{-1}$; 3466,2952,2869,1742,1660,1445,1439, 1399,1352,1284,1212, 1138,1048,943,756,706,579

EXAMPLE 29

(2E,11R,16R)-11,15-Dideoxy-11-(2-hydroxyethylthio)-16-hydroxy-17,17-trimethylene-2,3-didehydro-PGE$_1$ methyl ester (Compound 29) and (2E,11S,16R)-11,15-dideoxy-11-(2-hydroxyethylthio)-16-hydroxy-17,17-trimethylene-2,3-didehydro-PGE$_1$ methyl ester (Compound 30)

(1) Following the substantially same manner as in Example 1(2) using (4E)-5-methoxycarbonyl-4-pentenyl zinc (II) iodide in place of 5-methoxycarbonylpentyl zinc (II) iodide in Example 1(2), thereby (2E,16RS)-15-deoxy-16-hydroxy-17,17-trimethylene-2,3-didehydro-PGE$_1$ methyl ester 11,16-bis(tert-butyldimethylsilyl ether) was obtained.

$^1$H-NMR(CDCl$_3$,200 MHz) δ ppm; 0.04(s,3H),0.05(s, 3H),0.06(2s,6H),0.81–0.98(m,3H), 0.88(s,9H),0.91 and 0.92(2s,9H),1.14–2.69(m,24H),3.50–3.63(m,1H),3.73(s, 3H),3.90–4.09(m,1H),5.21–5.37(m,1H), 5.51–5.89(m,2H), 6.95(dt,J=15.8,6.8 Hz,1H)

IR(neat) cm$^{-1}$; 2955,2930,2857,1746,1728,1659,1472, 1464,1436,1361,1257, 1155,1095,1006,974,939,837,775, 670

(2) Following the substantially same manner as in Example 1(3) using the compound obtained in (1), thereby the compounds described below were obtained.

(2E,16R)-15-Deoxy-16-hydroxy-17,17-trimethylene-2,3-didehydro-PGE$_1$ methyl ester $^1$H-NMR(CDCl$_3$,300 MHz) δ ppm; 0.95(t,J=6.8 Hz,3H), 1.23–2.43(m,25H),2.69–2.81(m,1H), 3.54–3.63(m,1H),3.73 (s,3H),4.01–4.17(m,1H),5.40–5.54(m,1H),5.67–5.82(m, 1H),5.82(dt,J=15.7,1.6 Hz,1H), 6.95(dt,J=15.7,7.0 Hz,1H)

IR(neat) cm$^{-1}$; 3432,2930,2860,1740,1734,1654,1436, 1274,1202,1175,1076, 974,860,720

(2E,16S)-15-Deoxy-16-hydroxy-17,17-trimethylene-2,3-didehydro-PGE$_1$ methyl ester $^1$H-NMR(CDCl$_3$,300 MHz) δ ppm; 0.95(t,J=7.0 Hz,3H), 1.22–2.42(m,24H), 2.22(dd,J=18.3,9.6 Hz,1H),2.74(ddd,J= 18.3,7.6,1.1 Hz,1H), 3.57(dd,J=10.1,2.3 Hz,1H),3.72(s,3H), 3.98–4.10(m,1H), 5.38–5.49(m,1H),5.66–5.81(m,1H),5.81 (dt,J=15.6,1.6 Hz,1H), 6.94(dt,J=15.6,7.0 Hz,1H)

IR(neat) cm$^{-1}$; 3400,2930,2860,1740,1728,1436,1273, 1202,1158,1072,969, 876,720

(3) Following the substantially same manner as in Example 1(4) using (2E,16R)-15-deoxy-16-hydroxy-17,17-trimethylene-2,3-didehydro-PGE$_1$ methyl ester obtained in (2), thereby (2E,16R)-15-deoxy-16-hydroxy-17,17-trimethylene-2,3-didehydro-PGE$_1$ methyl ester was obtained.

$^1$H-NMR(CDCl$_3$,200 MHz) δ ppm; 0.94(t,J=6.9 Hz,3H), 1.16–2.32(m,22H),3.15–3.30(m,1H), 3.55(dd,J=9.8,2.7 Hz,1H),3.73(s,3H),5.49(dd,J=15.4,7.5 Hz, 1H), 5.66(ddd,J= 15.4,7.0,5.9 Hz,1H), 5.83(dt,J=15.6,1.6 Hz,1H),6.16(dd,J= 5.7,2.0 Hz,1H), 6.96(dt,J=15.6,7.0 Hz,1H),7.49(dd,J=5.7, 2.5 Hz,1H)

IR(neat) cm$^{-1}$; 3503,2930,2860,1708,1702,1654,1588, 1540,1457,1436,1346, 1314,1273,1199,1177,1070,1034, 977,930,870,805

(4) Following the substantially same manner as in Example 1(5) using the compound obtained in (3), thereby the title compounds were obtained.

Compound 29:

$^1$H-NMR(CDCl$_3$,200 MHz) δ ppm; 0.95(t,J=6.8 Hz,3H), 1.16–2.47(m,23H), 2.20(dd,J=18.6,11.0 Hz,1H),2.37(ddd, J=11.4,10.5,8.6 Hz,1H),2.81(dt,J=2.6,5.9 Hz,2H), 2.84(ddd, J=18.6,7.8,1.2 Hz,1H),3.04(ddd,J=11.0,10.5,7.8 Hz,1H), 3.59(dd,J=9.7,2.9 Hz,1H), 3.73(s,3H),3.74(t,J=5.9 Hz,2H), 5.47(dd,J=15.6,8.6 Hz,1H),5.61–5.88(m,1H),5.82(dt,J= 15.6,1.5 Hz,1H),6.95(dt,J=15.6,7.0 Hz,1H)

IR(neat) cm$^{-1}$; 3459,2930,2870,1740,1734,1654,1456, 1436,1402,1315,1278, 1202,1176,1045,975,930,876,848, 740,720,666

Compound 30:

$^1$H-NMR(CDCl$_3$,200 MHz) δ ppm; 0.95(t,J=6.8 Hz,3H), 1.16–2.44(m,23H),2.52–2.93(m,5H), 3.47–3.67(m,1H),3.58 (dd,J=9.8,2.3 Hz,1H),3.73(s,3H), 3.76(t,J=5.9 Hz,2H), 5.52–5.81(m,2H), 5.82(dt,J=15.6,1.5 Hz,1H),6.95(dt,J= 15.6,7.0 Hz,1H)

IR(neat) cm$^{-1}$; 3454,2930,2870,1740,1734,1654,1456, 1436,1401,1315,1278, 1202,1176,1046,980,930,876,848, 757,720,669

EXAMPLE 30

(2E,11R,16R)-11,15-Dideoxy-11-(2-hydroxyethylthio)-16-hydroxy-17,17-trimethylene-2, 3-didehydro-PGE$_1$ (Compound 31)

To an aqueous suspension (20.8 ml) of lipase PS (3.70 g) were added an acetone solution (7.1 ml) of (2E,11R,16R)-11,15-dideoxy-11-(2-hydroxyethylthio)-16-hydroxy-17,17-trimethylene-2,3-didehydro-PGE$_1$ methyl ester obtained in Example 29 (153 mg), phosphate buffer solution (pH=7.0, 0.2 M, 3.56 ml) and water (50.9 ml), followed by stirring at 30° C. overnight. The reaction solution was filtered, and the filtrate was adjusted to pH 5 with 1 N hydrochloric acid, salted out with ammonium sulfate and extracted with ethyl acetate. The organic layer was washed with a saturated aqueous sodium chloride solution, dried over anhydrous magnesium sulfate and filtered. The filtrate was concentrated under reduced pressure, and the resulting crude product was purified by a silica gel column chromatography (developing solvent; hexane:ethyl acetate=1:2 to ethyl acetate) to give the title compound (92 mg).

$^1$H-NMR(CDCl$_3$,300 MHz) δ ppm; 0.94(t,J=6.8 Hz,3H), 1.18–2.46(m,24H), 2.20(dd,J=18.7,11.2 Hz,1H),2.62–3.15 (m,5H), 3.60(dd,J=9.7,2.7 Hz,1H),3.74(t,J=5.9 Hz,2H), 5.47 (dd,J=15.3,8.9 Hz,1H),5.63–5.90(m,2H), 7.03(dt,J=15.5,7.0 Hz,1H)

IR(neat) cm$^{-1}$; 3414,2930,2870,1740,1702,1654,1466, 1424,1402,1283,1246, 1218,1202,1065,1047,1012,976,930, 876,854,757,666

EXAMPLE 31

(2E,11R,16S)-11,15-Dideoxy-11-(2-hydroxyethylthio)-16-hydroxy-17,17-trimethylene-2, 3-didehydro-PGE$_1$ methyl ester (Compound 32) and (2E,11S,16S)-11,15-dideoxy-11-(2-hydroxyethylthio)-16-hydroxy-17,17-trimethylene-2, 3-didehydro-PGE$_1$ methyl ester (Compound 33)

(1) Following the substantially same manner as in Example 1(4) using (2E,16S)-15-deoxy-16-hydroxy-17,17-trimethylene-2,3-didehydro-PGE$_1$ methyl ester obtained in Example 29(2), thereby (2E,16S)-15-deoxy-16-hydroxy-17, 17-trimethylene-2,3-didehydro-PGE$_1$ methyl ester was obtained.

$^1$H-NMR(CDCl$_3$,200 MHz) δ ppm; 0.94(t,J=6.9 Hz,3H), 1.18–2.44(m,22H),3.15–3.30(m,1H), 3.55(dd,J=9.7,2.6 Hz,1H),3.73(s,3H),5.47(dd,J=15.2,8.1 Hz, 1H),5.68(dt,J= 15.2,6.9 Hz,1H),5.83(dt,J=15.7,1.5 Hz,1H), 6.15(dd,J=5.7, 2.0 Hz,1H),6.96(dt,J=15.7,7.0 Hz,1H), 7.48(dd,J=5.7,2.5 Hz,1H)

IR(neat) cm$^{-1}$; 3468,2931,2860,1708,1702,1654,1588, 1456,1436,1384,1346, 1314,1273,1199,1176,1034,977,930, 870,806,719

(2) Following the substantially same manner as in Example 1(5) using the compound obtained in (1), thereby the title compounds were obtained.

Compound 32:

$^1$H-NMR(CDCl$_3$,200 MHz) δ ppm; 0.94(t,J=6.8 Hz,3H), 1.12–2.46(m,24H), 2.20(dd,J=18.3,11.1 Hz,1H),2.54–3.16 (m,2H), 2.80(dt,J=4.4,5.9 Hz,1H),3.57(dd,J=10.2,2.1 Hz,1H), 3.73(s,3H),3.74(t,J=5.9 Hz,2H),5.41(dd,J=15.1,9.1 Hz,1H), 5.67(ddd,J=15.1,9.4,5.4 Hz,1H),5.81(dt,J=15.6,1.5 Hz,1H), 6.95(dt,J=15.6,7.0 Hz,1H)

IR(neat) cm$^{-1}$; 3448,2930,2870,1740,1734,1654,1456, 1436,1402,1385,1314, 1274,1201,1176,1062,1045,974,930, 876,848,720

Compound 33:

$^1$H-NMR(CDCl$_3$,200 MHz) δ ppm; 0.94(t,J=6.8 Hz,3H), 1.16–2.94(m,26H), 2.75(dt,J=11.9,5.8 Hz,2H),3.47–3.67(m, 1H), 3.54(dd,J=10.3,2.2 Hz,1H),3.73(s,3H),3.76(t,J=5.8 Hz,2H), 5.55–5.89(m,2H),5.81(dt,J=15.7,1.5 Hz,1H), 6.95 (dt,J=15.7,7.0 Hz,1H)

IR(neat) cm$^{-1}$; 3459,2930,2870,1740,1734,1654,1436, 1401,1315,1278,1202, 1175,1046,979,930,876,848,720,670

EXAMPLE 32

(2E,11R,16S)-11,15-Dideoxy-11-(2-hydroxyethylthio)-16-hydroxy-17,17-trimethylene-2, 3-didehydro-PGE$_1$ (Compound 34)

Following the substantially same manner as in Example 30 using (2E,11R,16S)-11,15-dideoxy-11-(2-hydroxyethylthio)-16-hydroxy-17,17-trimethylene-2,3-didehydro-PGE$_1$ methyl ester obtained in Example 31, thereby the title compound was obtained.

$^1$H-NMR(CDCl$_3$,300 MHz) δ ppm; 0.94(t,J=6.8 Hz,3H), 1.21–2.45(m,25H), 2.20(dd,J=18.7,11.2 Hz,1H),2.66–3.12 (m,3H), 2.80(dt,J=9.8,5.9 Hz,1H),3.57(dd,J=10.5,2.3 Hz,1H), 3.74(t,J=5.9 Hz,2H),5.42(dd,J=14.8,8.6 Hz,1H), 5.66(ddd,J=14.8,9.7,5.2 Hz,1H),5.81(dt,J=15.5,1.5 Hz,1H), 7.04(dt,J=15.5,7.0 Hz,1H)

IR(neat) cm$^{-1}$; 3436,2930,2870,1740,1697,1648,1466, 1424,1402,1283,1223, 1180,1065,1049,974,930,876,756, 670

EXAMPLE 33

(11R,16R)-3-Thia-11,15-dideoxy-11-(2-hydroxyethylthio)-16-hydroxy-17,17-trimethylene-PGE$_1$ methyl ester (Compound 79) and (11S,16R)-3-thia-11,15-dideoxy-11-(2-hydroxyethylthio)-16-hydroxy-17,17-trimethylene-PGE$_1$ methyl ester (Compound 80)

(1) Following the substantially same manner as in Example 1(2) using 5-methoxycarbonyl-4-thiapentyl zinc (II) iodide in place of 5-methoxycarbonylpentyl zinc (II) iodide in Example 1(2), thereby (16RS)-3-thia-15-deoxy-16-hydroxy-17,17-trimethylene-PGE$_1$ methyl ester 11,16-bis(tert-butyldimethylsilyl ether) was obtained.

$^1$H-NMR(CDCl$_3$,200 MHz) δ ppm; 0.04(s,3H),0.05(s, 3H),0.06(s,3H),0.07(s,3H),0.70–1.03(m,3H),0.88(s,9H), 0.91 and 0.92(2s,9H),1.13–2.24(m,19H),2.16(dd,J=18.0,8.1 Hz,1H),2.32–2.82(m,4H),3.21(s,2H),3.51–3.63(m,1H),3.74 (s,3H),3.90–4.08(m,1H), 5.20–5.38(m,1H),5.52–5.74(m, 1H)

IR(neat) cm$^{-1}$; 2955,2930,2857,1746,1472,1436,1385, 1257,1094,1007,939,837,775,670

(2) Following the substantially same manner as in Example 1(3) using the compound obtained in (1), thereby the compounds described below were obtained.

(16R)-3-Thia-15-deoxy-16-hydroxy-17,17-trimethylene-PGE$_1$ methyl ester $^1$H-NMR(CDCl$_3$,300 MHz) δ ppm; 0.94(t,J=7.0 Hz,3H), 1.23–2.13(m,20H),2.17–2.43(m,2H), 2.23(dd,J=18.5,9.6 Hz,1H),2.52–2.81(m,2H), 2.75(ddd,J=18.5,7.5,1.2 Hz,1H), 3.22(bs,2H),3.59(dd,J=9.9, 2.6 Hz,1H),3.74(s,3H), 4.01–4.13(m,1H), 5.48(dd,J=15.2,8.6 Hz,1H),5.75(ddd,J= 15.2,8.2,6.2 Hz,1H).

IR(neat) cm$^{-1}$; 3432,2952,2930,2870,1740,1734,1456, 1436,1284,1154,1073, 1011,971,594

(16S)-3-Thia-15-deoxy-16-hydroxy-17,17-trimethylene-PGE$_1$ methyl ester $^1$H-NMR(CDCl$_3$,300 MHz) δ ppm; 0.95(t,J=6.8 Hz,3H), 1.22–2.11(m,20H), 2.23(dd,J=18.5,9.5 Hz,1H),2.23–2.42 (m,1H), 2.36(dt,J=12.3,8.7 Hz,1H),2.54–2.70(m,2H), 2.74 (ddd,J=18.5,7.4,1.1 Hz,1H),3.22(s,2H),3.58(dd,J=10.3, 2.6 Hz,1H), 3.74(s,3H),4.04(ddd,J=9.5,8.7,7.4 Hz,1H), 5.44(dd, J=14.8,8.7 Hz,1H),5.67–5.83(m,1H)

IR(neat) cm$^{-1}$; 3400,2952,2930,2870,1740,1734,1456, 1436,1283,1154,1075, 1011,968,876,736

(3) Following the substantially same manner as in Example 1(4) using (16R)-3-thia-15-deoxy-16-hydroxy-17, 17-trimethylene-PGE$_1$ methyl ester obtained in (2), thereby (16R)-3-thia-15-deoxy-16-hydroxy-17,17-trimethylene-PGE$_1$ methyl ester was obtained.

$^1$H-NMR(CDCl$_3$,200 MHz) δ ppm; 0.94(t,J=6.9 Hz,3H), 1.18–2.32(m,19H),2.55–2.76(m,1H), 2.65(t,J=7.0 Hz,2H), 3.18–3.31(m,1H),3.23(s,2H), 3.56(dd,J=9.8,2.7 Hz,1H), 3.74(s,3H),5.49–5.75(m,1H), 5.50(dd,J=15.4,7.7 Hz,1H), 6.16(dt,J=5.7,2.2 Hz,1H), 7.49(dd,J=5.7,2.5 Hz,1H)

IR(neat) cm$^{-1}$; 3497,2930,2860,1735,1702,1588,1436, 1384,1351,1279,1133, 1070,1010,972,930,880,800

(4) Following the substantially same manner as in Example 1(5) using the compound obtained in (3), thereby the title compounds were obtained.

Compound 79:

$^1$H-NMR(CDCl$_3$,200 MHz) δ ppm; 0.85–1.06(m,3H), 1.18–2.50(m,22H), 2.20(dd,J=18.3,11.1 Hz,1H),2.62(t,J= 6.8 Hz,2H),2.72–3.13(m,4H),3.22(s,2H),3.60(dd,J=9.7,2.6 Hz,1H),3.69–3.84(m,2H),3.74(s,3H),5.47(dd,J=15.2,8.6 Hz,1H), 5.75(ddd,J=15.2,7.7,6.3 Hz,1H)

IR(neat) cm$^{-1}$; 3460,2952,2930,2870,1740,1734,1456, 1436,1406,1283,1217, 1190,1154,1148,1062,1046,1011, 971,930,876

Compound 80:

$^1$H-NMR(CDCl$_3$,200 MHz) δ ppm; 0.94(t,J=6.8 Hz,3H), 1.14–2.94(m,28H),3.22(s,2H),3.48–3.66(m,2H),3.74(s,3H), 3.76(t,J=5.8 Hz,2H),5.51–5.80(m,2H)

IR(neat) cm$^{-1}$; 3436,2952,2930,2870,1740,1734,1456, 1436,1402,1283,1218, 1195,1158,1137,1062,1046,1011, 974

EXAMPLE 34

(11R,16R)-3-Thia-11,15-dideoxy-11-(2-hydroxyethylthio)-16-hydroxy-17,17-trimethylene-PGE$_1$ (Compound 81)

Following the substantially same manner as in Example 2 using (11R,16R)-3-thia-11,15-dideoxy-1-(2-hydroxyethylthio)-16-hydroxy-17,17-trimethylene-PGE$_1$ methyl ester obtained in Example 33, thereby the title compound was obtained.

$^1$H-NMR(CDCl$_3$,200 MHz) δ ppm; 0.94(t,J=6.7 Hz,3H), 1.20–4.26(m,25H),2.20(dd,J=18.5,11.0 Hz,1H),2.66(t,J=6.2 Hz,2H), 2.81(t,J=5.9,2H),2.83(ddd,J=18.5,7.9,1.2 Hz,1H), 3.19(s,1H),3.75(t,J=5.9 Hz,2H),5.44(dd,J=15.2,8.6 Hz,1H), 5.75(ddd,J=15.2,8.4,5.6 Hz,1H)

IR(neat) cm $^{-1}$; 3436,2930,2870,1740,1734,1456,1402, 1352,1284,1179,1153, 1062,1047,1009,970,931,876,670

EXAMPLE 35

(11R,16S)-3-Thia-11,15-dideoxy-11-(2-hydroxyethylthio)-16-hydroxy-17,17-trimethylene-PGE$_1$ methyl ester (Compound 82) and (11S,16S)-3-thia-11,15-dideoxy-11-(2-hydroxyethylthio)-16-hydroxy-17,17-trimethylene-PGE$_1$ methyl ester (Compound 83)

(1) Following the substantially same manner as in Example 1(4) using (16S)-3-thia-15-deoxy-16-hydroxy-17,17-trimethylene-PGE$_1$ methyl ester obtained in Example 33(2), thereby (16S)-3-thia-15-deoxy-16-hydroxy-17,17-trimethylene-PGE$_1$ methyl ester was obtained.

$^1$H-NMR(CDCl$_3$,200 MHz) δ ppm; 0.94(t,J=6.8 Hz,3H), 1.21–2.32(m,19H),2.60–2.84(m,3H), 3.14–3.32(m,1H),3.23 (bs,2H),3.56(dd,J=9.7,2.6 Hz,1H), 3.74(s,3H),5.48(dd,J= 15.4,8.1 Hz,1H),5.58–5.80(m,1H), 6.15(dt,J=5.7,2.0 Hz,1H), 7.49(dd,J=5.7,2.4 Hz,1H)

IR(neat) cm$^{-1}$; 3486,2930,2860,1740,1702,1588,1436, 1346,1279,1133,1009, 972

(2) Following the substantially same manner as in Example 1(5) using the compound obtained in (1), thereby the title compounds were obtained.

Compound 82:

$^1$H-NMR(CDCl$_3$,200 MHz) δ ppm; 0.94(t,J=6.7 Hz,3H), 1.16–2.47(m,22H), 2.20(dd,J=18.5,11.0 Hz,1H),2.55–3.12 (m,4H), 2.62(t,J=7.0 Hz,2H),3.22(s,2H),3.57(dd,J=10.3,2.0 Hz,1H), 3.65–3.85(m,2H),3.74(s,3H),5.42(dd,J=15.2,8.4 Hz,1H), 5.68(ddd,J=15.2,9.3,5.5 Hz,1H)

IR(neat) cm$^{-1}$; 3460,2952,2930,2870,1740,1735,1457, 1436,1406,1396,1282, 1218,1153,1137,1065,1049,1011, 970,930,876,741

Compound 83:

$^1$H-NMR(CDCl$_3$,200 MHz) δ ppm; 0.94(t,J=6.8 Hz,3H), 1.20–2.16(m,19H),2.22–2.96(m,5H), 2.62(t,J=7.0 Hz,2H), 2.75(dt,J=11.6,5.7 Hz,2H),3.22(s,2H), 3.48–3.66(m,1H), 3.54(dd,J=10.3,2.2 Hz,1H),3.74(s,3H), 3.76(t,J=5.7 Hz,2H), 5.53–5.82(m,2H)

IR(neat) cm$^{-1}$; 3436,2952,2930,2870,1740,1734,1456, 1436,1402,1283,1218, 1195,1158,1136,1065,1046,1011, 974,876,742,590

EXAMPLE 36

(11R,16S)-3-Thia-11,15-dideoxy-11-(2-hydroxyethylthio)-16-hydroxy-17,17-trimethylene-PGE$_1$ (Compound 84)

Following the substantially same manner as in Example 2 using (11R,16S)-3-thia-11,15-dideoxy-11-(2-hydroxyethylthio)-16-hydroxy-17,17-trimethylene-PGE$_1$ methyl ester obtained in Example 35, thereby the title compound was obtained.

$^1$H-NMR(CDCl$_3$,200 MHz) δ ppm; 0.95(t,J=6.8 Hz,3H), 1.16–2.52(m,20H),2.21(dd,J=18.3,11.1 Hz,1H),2.53–4.00 (m,7H), 2.81(dt,J=2.5,5.9 Hz,2H),3.18(d,J=14.9 Hz,1H), 3.26(d,J=14.9 Hz,1H),3.63(dd,J=10.4,2.1 Hz,1H), 3.75(t,J= 5.9 Hz,2H),5.45(dd,J=15.3,8.7 Hz,1H),5.74(ddd,J=15.3,8.4, 6.4 Hz, 1H)

IR(neat) cm$^{-1}$; 3436,2930,1734,1456,1424,1402,1284, 1179,1158,1049,1009,971,930,876,757,670

EXAMPLE 37

(11R,16R)-6-Thia-11,15-dideoxy-11-(2-hydroxyethylthio)-16-hydroxy-17,17-trimethylene-PGE$_1$ methyl ester (Compound 118)

(1) To a toluene solution (2.0 ml) of the compound obtained in Example 1(1) (1.03 g) was added methyl 5-mercaptopentanoate (363 mg) at room temperature, followed by stirring at room temperature overnight. Subsequently, duisopropylamine (3 μl) was added, followed by stirring at room temperature for 3 hours. The reaction solution was applied to a silica gel column chromatography (developing solvent; hexane:ethyl acetate=49:1 to 9:1) to give (16RS)-6-thia-15-deoxy-16-hydroxy-17,17-trimethylene-PGE$_1$ methyl ester 11,16-bis(tert-butyldimethylsilyl ether) (818 mg).

$^1$H-NMR(CDCl$_3$,200 MHz) δ ppm; 0.04(s,3H),0.06(s, 3H),0.07(2s,6H),0.75–1.02(m,3H), 0.88(s,9H),0.91 and 0.92(2s,9H),1.16–2.38(m,20H),2.41–2.93(m,4H),2.50(t,J= 6.9 Hz,2H),3.52–3.76(m,1H), 3.67(s,3H),3.98–4.13(m,1H), 5.24–5.42(m,1H),5.52–5.77(m,1H)

IR(neat) cm$^{-1}$; 2955,2930,2857,1746,1472,1435,1361, 1257,1154,1089,1006, 939,836,775,669

(2) Following the substantially same manner as in Example 1(3) using the compound obtained in (1), thereby the compounds described below were obtained.

(16R)-6-Thia-15-deoxy-16-hydroxy-17,17-trimethylene-PGE$_1$ methyl ester $^1$H-NMR(CDCl$_3$,300 MHz) δ ppm; 0.94(t,J=6.8 Hz,3H), 1.23–2.11(m,18H),2.24–2.36(m,2H), 2.28(dd,J=18.5,9.3 Hz,1H),2.33(t,J=7.2 Hz,2H),2.52(t,J=7.2 Hz,2H),2.58–2.70 (m,1H),2.71–2.90(m,3H), 3.58(dd,J=10.2,2.4 Hz,1H),3.67 (s,3H),4.06–4.17(m,1H), 5.47–5.52(m,1H),5.70–5.83(m, 1H)

IR(neat) cm$^{-1}$; 3436,2952,2930,2870,1740,1436,1277, 1208,1158,1073,973, 757

(16S)-6-Thia-15-deoxy-16-hydroxy-17,17-trimethylene-PGE$_1$ methyl ester $^1$H-NMR(CDCl$_3$,300 MHz) δ ppm; 0.94(t,J=6.9 Hz,3H), 1.23–2.12(m,17H),2.24–2.36(m,2H), 2.27(dd,J=18.3,9.4 Hz,1H),2.33(t,J=7.2 Hz,2H),2.47–2.58(m,2H),2.62–2.90(m, 4H),3.59(dd,J=9.6,2.4 Hz,1H), 3.67(s,3H),4.04–4.17(m, 1H),5.48(dd,J=15.2,8.2 Hz,1H), 5.72–5.84(m,1H)

IR(neat) cm$^{-1}$; 3400,2952,2871,1740,1436,1342,1262, 1207,1158,1076,969, 877,806

(3) Following the substantially same manner as in Example 1(4) using (16R)-6-thia-15-deoxy-16-hydroxy-17,17-trimethylene-PGE$_1$ methyl ester obtained in the above (2), thereby (16R)-6-thia-15-deoxy-16-hydroxy-17,17-trimethylene-PGE$_1$ methyl ester was obtained.

$^1$H-NMR(CDCl$_3$+D$_2$O,200 MHz) δ ppm; 0.94(t,J=6.8 Hz,3H),1.20–2.12(m,14H),2.16–2.40(m,2H), 2.33(t,J=6.9 Hz,2H),2.46–2.62(m,1H),2.54(t,J=7.0 Hz,2H), 2.66(dd,J= 12.7,9.0 Hz,1H),3.02(dd,J=12.7,4.2 Hz,1H),3.46–3.63(m, 2H),3.68(s,3H),5.47–5.78(m,1H), 5.55(dd,J=15.8,7.0 Hz,1H),6.19(dd,J=5.8,2.2 Hz,1H), 7.56(dd,J=5.8,2.5 Hz,1H)

IR(neat) cm$^{-1}$; 3480,2952,2870,1740,1708,1584,1436, 1352,1273,1174,1070, 972,800

(4) Following the substantially same manner as in Example 1(5) using the compound obtained in the above (3), thereby the title compound was obtained.

$^1$H-NMR(CDCl$_3$,200 MHz) δ ppm; 0.94(t,J=6.8 Hz,3H), 1.20–2.15(m,18H),2.20–2.40(m,1H), 2.24(dd,J=18.5,11.2 Hz,1H),2.33(t,J=6.9 Hz,2H),2.44–3.32(m,9H),2.51(t,J=6.7 Hz,2H),3.58(dt,J=9.9,2.7 Hz,1H), 3.67(s,3H),3.75(dt,J=2.1, 5.9 Hz,2H),5.41–5.86(m,2H)

IR(neat) cm$^{-1}$; 347012952,2930,2870,1740,1735,1436, 1376,1294,1277,1208, 1174,1066,1046,971,876,746

EXAMPLE 38

(11R,16R)-6-Thia-11,15-dideoxy-11-(2-hydroxyethylthio)-16-hydroxy-17,17-trimethylene-PGE$_1$ (Compound 119)

Following the substantially same manner as in Example 2 using the compound obtained in Example 37, thereby the title compound was obtained.

$^1$H-NMR(CDCl$_3$,200 MHz) δ ppm; 0.94(t,J=6.8 Hz,3H), 1.21–2.18(m,16H),2.20–4.21(m,13H), 2.24(dd,J=18.5,11.2 Hz,1H),2.37(t,J=6.8 Hz,2H), 3.63(dd,J=10.1,2.4 Hz,1H), 3.75(t,J=5.9 Hz,2H), 5.48(dd,J=15.3,8.7 Hz,1H),5.78(ddd, J=15.3,7.8,5.9 Hz,1H)

IR(neat) cm$^{-1}$; 3400,2930,2870,1740,1734,1456,1402, 1283,1218,1179,1158, 1066,1046,971,930,876,757

EXAMPLE 39

(11R,16S)-6-Thia-11,15-dideoxy-11-(2-hydroxyethylthio)-16-hydroxy-17,17-trimethylene-PGE$_1$ methyl ester (Compound 120)

(1) Following the substantially same manner as in Example 1(4) using (16S)-6-thia-15-deoxy-16-hydroxy-17,17-trimethylene-PGE$_1$ methyl ester obtained in Example 37(2), thereby (16S)-6-thia-15-deoxy-16-hydroxy-17,17-trimethylene-PGE$_1$ methyl ester was obtained.

$^1$H-NMR(CDCl$_3$,200 MHz) δ ppm; 0.94(t,J=6.9 Hz,3H), 1.14–2.12(m,15H),2.16–2.40(m,2H), 2.33(t,J=7.3 Hz,2H), 2.44–2.60(m,1H),2.54(t,J=6.9 Hz,2H), 2.68(dd,J=12.9,8.6 Hz,1H),3.00(dd,J=12.9,4.2 Hz,1H),3.46–3.62(m,2H),3.67 (s,3H),5.48–5.80(m,1H), 5.55(dd,J=15.5,7.4 Hz,1H),6.19 (dd,J=5.7,2.2 Hz,1H), 7.56(dd,J=5.7,2.5 Hz,1H)

IR(neat) cm$^{-1}$; 3468,2952,2870,1740,1708,1584,1436, 1351,1274,1205,1174, 1070,1031,972

(2) Following the substantially same manner as in Example 1(5) using the compound obtained in the above (1), thereby the title compound was obtained.

$^1$H-NMR(CDCl$_3$,200 MHz) δ ppm; 0.94(t,J=6.8 Hz,3H), 1.18–2.13(m,19H),2.21–2.40(m,1H), 2.24(dd,J=18.7,11.2 Hz,1H),2.33(t,J=7.1 Hz,2H),2.44–3.32(m,7H), 2.51(t,J=7.0 Hz,2H), 3.57(ddd,J=10.2,4.3,2.5 Hz,1H),3.67(s,3H), 3.76 (dt,J=2.5,5.8 Hz,1H),5.35–5.83(m,2H)

IR(neat) cm$^{-1}$; 3459,2952,2870,1740,1456,1436,1278, 1208,1174,1066,1050, 971,876

EXAMPLE 40

(11R,16S)-6-Thia-11,15-dideoxy-11-(2-hydroxyethylthio)-16-hydroxy-17,17-trimethylene-PGE$_1$ (Compound 121)

Following the substantially same manner as in Example 2 using the compound obtained in Example 39, thereby the title compound was obtained.

$^1$H-NMR(CDCl$_3$,300 MHz) δ ppm; 0.94(t,J=6.8 Hz,3H), 1.20–2.13(m,17H),2.13–2.44(m,1H), 2.25(dd,J=18.5,11.2 Hz,1H),2.37(t,J=6.9 Hz,2H),2.45–3.15(m,11H), 3.60(dd,J= 10.2,2.3 Hz,1H),3.75(t,J=5.9 Hz,2H), 5.44(dd,J=15.2,9.2 Hz,1H),5.75(ddd,J=15.2,9.0,5.9 Hz,1H)

IR(neat) cm$^{-1}$; 3436,2930,2870,1740,1730,1456,1402, 1284,1218,1180,1158, 1065,1046,970,935,876,757,670

Experiment [Determination of DNA synthesis inhibition activity of PGE$_1$ derivatives to human vascular smooth muscle cells]

On a 24-well plate (manufactured by Corning Co.), 1×10$^4$ cells/well of quintic culture cells of vascular cells derived from normal human aorta (produced by Kurabo Co.) were inoculated and cultured for 2 days. The medium was exchanged from the growth medium (SG2: produced by Kurabo Co.) to the basal medium (SB2: produced by Kurabo Co.), and cultured for 24 hours, to which was added the growth medium (SG2) containing an ethanol solution of the test compound. $^3$H-Thymidine (produced by Daiichi Chemicals Co.) was added in an amount of 0.01 mci/well and, after culturing for 24 hours, the cultured supernatant was removed by suction, followed by washing with a phosphate buffer solution (PBS). 5% Trichloroacetic acid (TCA) was added and, after allowing to stand at 4° C. for 20 minutes, the mixture was washed once with TCA. The mixture was washed with PBS, and dissolved in 0.5 M aqueous potassium hydroxide solution. Intake of $^3$H-thymidine was determined using 20 μl of the aqueous potassium hydroxide solution dissolving the cells which incorporated $^3$H-thymidine in the nucleus by means of a liquid scintillation counter (manufactured by Hewlett-Packard Co.).

Results are shown in Table 1.

TABLE 1

| 1 × 10$^{-5}$ M (Concentration of the compound added) | Growth inhibition rate (per cent to control) |
| --- | --- |
| Compound 23 | 91.5 |
| Compound 29 | 100 |
| Compound 32 | 100 |
| Compound 41 | 93.2 |
| Compound 54 | 100 |
| Compound 55 | 94.3 |

Note: The test compounds were each used as an ethanol solution and compared with a vehicle-treated group as control.

As a result, Compounds 23, 29, 32, 41, 54 and 55 were found to exhibit a high inhibiting activity on the growth of human vascular smooth muscle cells.

Industrial Applicability

The present invention provides PG derivatives which exhibit an excellent action in inhibiting the growth of vascular smooth muscle cells. The PG derivatives of the present invention are useful as drugs for prevention or treatment of vascular thickening which leads to the restenosis after percutaneous transluminal coronary angioplasty and vascular occlusion.

What is claimed is:

1. A prostaglandin derivative represented by the formula:

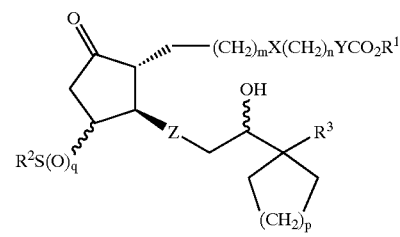

[wherein X is CH$_2$, O or a group represented by the formula: S(O)$_{q1}$ (wherein q1 is an integer of 0 to 2), Y is an ethylene group, a vinylene group, an ethynylene group or a group represented by the formula: O(CH$_2$)$_{t1}$ or S(O)$_{q2}$(CH$_2$)$_{t1}$ (wherein q2 is an integer of 0 to 2, and t1 is an integer of 1 to 3), Z is an ethylene group, a vinylene group or an ethynylene group, $R^1$ is a hydrogen atom, a $C_{1-10}$ alkyl group or a $C_{3-10}$ cycloalkyl group, $R^2$ is a $C_{1-10}$ alkyl group, a $C_{2-10}$ alkenyl group, a $C_{2-10}$ alkynyl group, a $C_{3-10}$ cycloalkyl group, a $C_{1-5}$ alkyl-$C_{3-10}$ cycloalkyl group, a $C_{3-10}$ cycloalkyl-$C_{1-5}$ alkyl group, a hydroxy-$C_{1-5}$ alkyl group, a halogeno-$C_{1-5}$ alkyl group, a $C_{1-5}$ alkoxy-$C_{1-5}$ alkyl group, a $C_{2-4}$ alkoxycarbonyl-$C_{1-5}$ alkyl group, a carboxyl-$C_{1-5}$ alkyl group, a cyano-$C_{1-5}$ alkyl group, a $C_{1-5}$ alkyl group substituted with a group represented by the formula: —$NR^7R^8$ (wherein $R^7$ and $R^8$ are the same or different, and each a hydrogen atom or a $C_{1-5}$ alkyl group, or $R^7$ and $R^8$ together with the nitrogen atom to which they are attached form a pyrrolidino group, a piperidino group, a piperazino group, a morpholino group or a thiomorpholino group), an acyl group, a group represented by the formula: —$(CH_2)_{t2}CH(NH_2)COOR^9$ (wherein $R^9$ is a hydrogen atom or a $C_{1-5}$ alkyl group, t2 is 1 or 2) or a group represented by the formula:

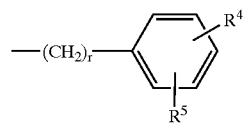

(wherein $R^4$ and $R^5$ are the same or different, and each a hydrogen atom, a hydroxyl group, a halogen atom, a $C_{1-10}$ alkyl group, a $C_{1-10}$ alkoxy group, a $C_{2-10}$ alkenyl group, a $C_{2-10}$ alkynyl group, a hydroxy-$C_{1-5}$ alkyl group, a halogeno-$C_{1-5}$ alkyl group, a $C_{1-5}$ alkoxy-$C_{1-5}$ alkyl group, a $C_{2-4}$ alkoxycarbonyl group, a carboxyl group, an acyl group, a nitro group, an amino group or an amino group which is mono- or di-substituted with $C_{1-5}$ alkyl group(s), and r is an integer of 0 to 3), $R^3$ is a hydrogen atom, a $C_{1-10}$ alkyl group, a $C_{3-10}$ cycloalkyl group, a $C_{1-5}$ alkyl-$C_{3-10}$ cycloalkyl group, a $C_{3-10}$ cycloalkyl-$C_{1-5}$ alkyl group, a $C_{2-10}$ alkenyl group or a $C_{2-10}$ alkynyl group, m is an integer of 0 to 3, n is an integer of 1 to 3, p is an integer of 0 to 5, and q is an integer of 0 to 2], a pharmaceutically acceptable salt thereof or a hydrate thereof.

2. The prostaglandin derivative according to claim 1 wherein X is $CH_2$ or a group represented by the formula: $S(O)_{q1}$ (wherein q1 is an integer of 0 to 2), $R^2$ is a $C_{1-10}$ alkyl group, a hydroxy-$C_{1-5}$ alkyl group, a $C_{1-5}$ alkoxy-$C_{1-5}$ alkyl group, a $C_{2-4}$ alkoxycarbonyl-$C_{1-5}$ alkyl group, a cyano-$C_{1-5}$ alkyl group, a $C_{1-5}$ alkyl group substituted with a group represented by the formula: —$NR^{77}R^{88}$ (wherein $R^{77}$ and $R^{88}$ are the same or different, and each a hydrogen atom or a $C_{1-5}$ alkyl group), a $C_{2-10}$ alkanoyl group, a group represented by the formula: —$(CH_2)_{t2}CH(NH_2)COOR^9$ (wherein $R^9$ is a hydrogen atom or a $C_{1-5}$ alkyl group, and t2 is 1 or 2) or a group represented by the formula:

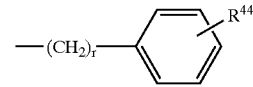

(wherein $R^{44}$ is a hydrogen atom, a halogen atom, a $C_{1-10}$ alkyl group, a $C_{1-10}$ alkoxy group, a nitro group or an amino group, and r is an integer of 0 to 3), and $R^3$ is a hydrogen atom, a $C_{1-10}$ alkyl group, a $C_{3-10}$ cycloalkyl group, a $C_{3-10}$ cycloalkyl-$C_{1-5}$ alkyl group or a $C_{2-10}$ alkenyl group; the pharmaceutically acceptable salt thereof or the hydrate thereof.

3. The prostaglandin derivative according to claim 1 wherein X is $CH_2$, Y is an ethylene group, a vinylene group, or a group represented by the formula: $O(CH_2)_{t1}$ or $S(O)_{q2}(CH_2)_{t1}$ (wherein q2 is an integer of 0 to 2, and t1 is an integer of 1 to 3), Z is a vinylene group or an ethynylene group, $R^1$ is a hydrogen atom or a $C_{1-10}$ alkyl group, $R^2$ is a hydroxy-$C_{1-5}$ alkyl group, a $C_{2-4}$ alkoxycarbonyl-$C_{1-5}$ alkyl group, a $C_{1-5}$ alkyl group substituted with a di-$C_{1-5}$ alkylamino group, a $C_{2-10}$ alkanoyl group, a group represented by the formula: —$(CH_2)_{t2}CH(NH_2)COOR^9$ (wherein $R^9$ is a hydrogen atom or a $C_{1-5}$ alkyl group, and t2 is 1 or 2) or a group represented by the formula:

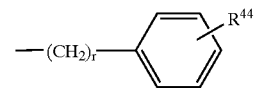

(wherein $R^{44}$ is a hydrogen atom, a halogen atom, a $C_{1-10}$ alkyl group, a $C_{1-10}$ alkoxy group, a nitro group or an amino group, and r is an integer of 0 to 3), and $R^3$ is a hydrogen atom or a $C_{1-10}$ alkyl group; the pharmaceutically acceptable salt thereof or the hydrate thereof.

4. The prostaglandin derivative according to claim 3 wherein $R^{44}$ is a hydrogen atom, a $C_{1-10}$ alkoxy group, a nitro group or an amino group; the pharmaceutically acceptable salt thereof or the hydrate thereof.

5. A pharmaceutical preparation which comprises as an effective ingredient the prostaglandin derivative according to any one of claims 1 to 4, the pharmaceutically acceptable salt thereof or the hydrate thereof.

6. The pharmaceutical preparation according to claim 5, which is a pharmaceutical preparation for prevention or treatment of the restenosis after PTCA.

* * * * *